(12) United States Patent
Hanko et al.

(10) Patent No.: US 10,036,098 B2
(45) Date of Patent: Jul. 31, 2018

(54) METHOD FOR DETERMINING AN ANALYTE CONTENT OF A LIQUID SAMPLE BY MEANS OF A BIOANALYZER

(75) Inventors: Michael Hanko, Dresden (DE); Angela Eubisch, Chemnitz (DE); Axel Fikus, Hartha (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 732 days.

(21) Appl. No.: 13/881,658

(22) PCT Filed: Aug. 26, 2011

(86) PCT No.: PCT/EP2011/064685
§ 371 (c)(1),
(2), (4) Date: Apr. 25, 2013

(87) PCT Pub. No.: WO2012/055606
PCT Pub. Date: May 3, 2012

(65) Prior Publication Data
US 2013/0213821 A1 Aug. 22, 2013

(30) Foreign Application Priority Data

Oct. 29, 2010 (DE) .................. 10 2010 043 153
Dec. 30, 2010 (DE) .................. 10 2010 064 391

(51) Int. Cl.
| | | |
|---|---|---|
| C25F 1/00 | (2006.01) | |
| G01N 33/52 | (2006.01) | |
| G01N 33/543 | (2006.01) | |
| G01N 33/569 | (2006.01) | |

(52) U.S. Cl.
CPC .............. C25F 1/00 (2013.01); G01N 33/52 (2013.01); G01N 33/5438 (2013.01); G01N 33/54306 (2013.01); G01N 33/56983 (2013.01)

(58) Field of Classification Search
None
See application file for complete search history.

(56) References Cited

U.S. PATENT DOCUMENTS

| | | | |
|---|---|---|---|
| 2009/0054255 A1 | 2/2009 | Lee et al. | |
| 2010/0240070 A1* | 9/2010 | Akhavan-Tafti | G01N 33/581 435/7.9 |
| 2013/0217003 A1* | 8/2013 | Hanko | G01N 33/54306 435/5 |

FOREIGN PATENT DOCUMENTS

| | | |
|---|---|---|
| EP | 1347300 A1 | 9/2003 |
| EP | 1413876 A2 | 4/2004 |
| WO | 9958963 A1 | 11/1999 |
| WO | 0062931 A1 | 10/2000 |
| WO | 0179848 A1 | 10/2001 |
| WO | 02093153 A1 | 11/2002 |
| WO | 03011768 A2 | 2/2003 |
| WO | 2008107649 A1 | 9/2008 |
| WO | 2009062027 A1 | 5/2009 |
| WO | 2010088219 A2 | 8/2010 |

OTHER PUBLICATIONS

Yang et al., "Integrated Microfluidic Device for Serum Biomarker Quantitation Using Either Standard Addition or a Calibration Curve", Anal. Chem., 2009, vol. 81, No. 19, pp. 8230-8235.*
Chah et al., "Surface plasmon resonance analysis of aqueous mercuric ions", Sensors and Actuators B: Chemical, 2004, vol. 99, issues 2-3, pp. 216-222.*
Nov. 8, 1011 International Search Report, The Netherlands.
Seokheun Choi, Junseok Chae; Reusable biosensors via in situ electrochemical surface regeneration in microfluidic applications; Biosensors and Bioelectronics; Apr. 10, 2009; 527-531; XP002662020; Arizona State University, Tempe, AZ.
Seokheun Choi et al; A regenerative biosensing surface in microfluidics using electrochemical desorption of short-chain self-assembled monolayer; Microfluid Nanofluid; 2009; 819-827; XP019745301; Arizona State University, Tempe, AZ.

(Continued)

*Primary Examiner* — Galina Yakovleva
(74) *Attorney, Agent, or Firm* — Christopher R. Powers; PatServe

(57) ABSTRACT

A method for automated in situ determining an analyte content of a liquid sample by means of a bioanalyzer, wherein a measurement duct has at least one substrate, comprising a repeatedly performable sequence of steps as follows: (i) preparing a sensor matrix, which has a plurality of receptors, which bind the analyte and/or a further target molecule, or bring about a chemical conversion of the analyte or of the further target molecule, leading through the measurement duct a preparation solution of at least a first chemical species, wherein a plurality of the first chemical species are bound on the substrate via the functional group binding on the substrate, wherein the other functional group of the plurality of the first chemical species bound on the substrate serves as a receptor or for subsequent binding of a receptor; (ii) leading the liquid sample, through the measurement duct, wherein analyte contained in the liquid sample or in the liquid to be measured, and/or other target molecules contained in the liquid sample or the liquid to be measured, bind, preferably selectively and specifically, on the receptors or are chemically converted by the receptors, and determining a measured variable correlated with the amount of the target molecules bound or converted by the receptors, and deriving therefrom the analyte content of the liquid sample; and (iii) regenerating, especially clearing, the at least one substrate, wherein the sensor matrix and, in given cases, molecules bound thereto, especially analyte molecules, other target molecules or other molecules, are released from the substrate and/or at least partially decomposed.

16 Claims, 6 Drawing Sheets

(56) References Cited

OTHER PUBLICATIONS

Canaria C A et al; Formation and removal of alkylthiolate self-assembled monolayers on gold in aqueous solutions; Lab on a Chip; The Royal Society of Chemistry; 2006; 289-295; XP002662021.
Tudos Anna J et al; Rapid Surface Plasmon Resonance-Based Inhibition Assay of Deoxynivalenol; Journal of Agricultural and Food Chemistry; Sep. 24, 2003; 5843-5848; XP002662022.
Mar. 31, 2011 German Search Report, Munchen, Germany.
May 10, 2013 English Translation of IPR, Geneva, Switzerland.

* cited by examiner

Fig. 3)
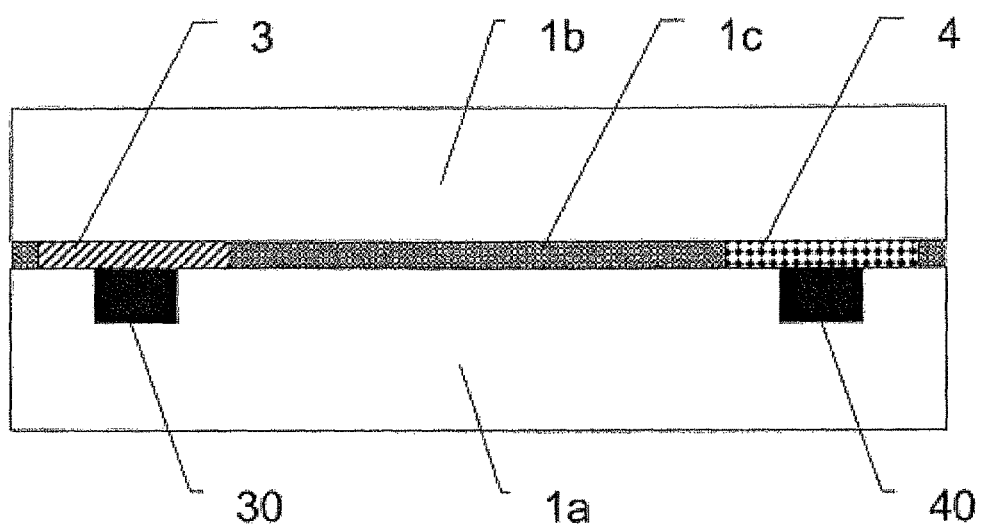
Microfluidic system (cross section on A-A of Fig. 2)

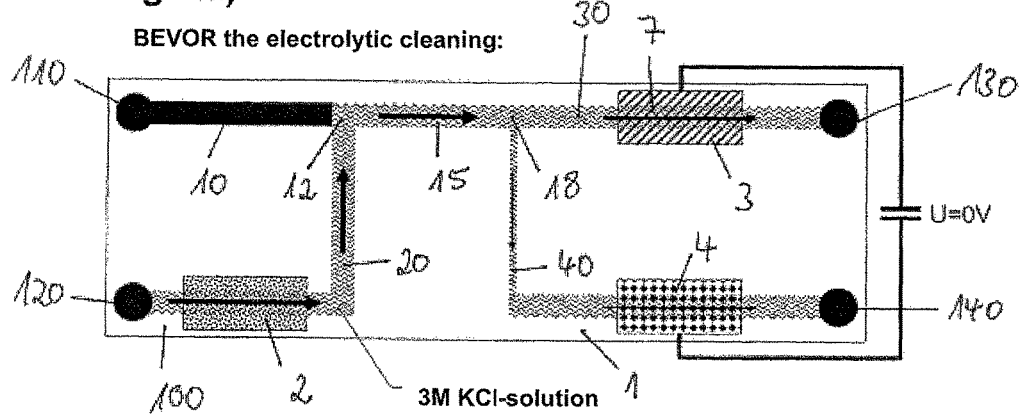
Fig. 4a) BEVOR the electrolytic cleaning:
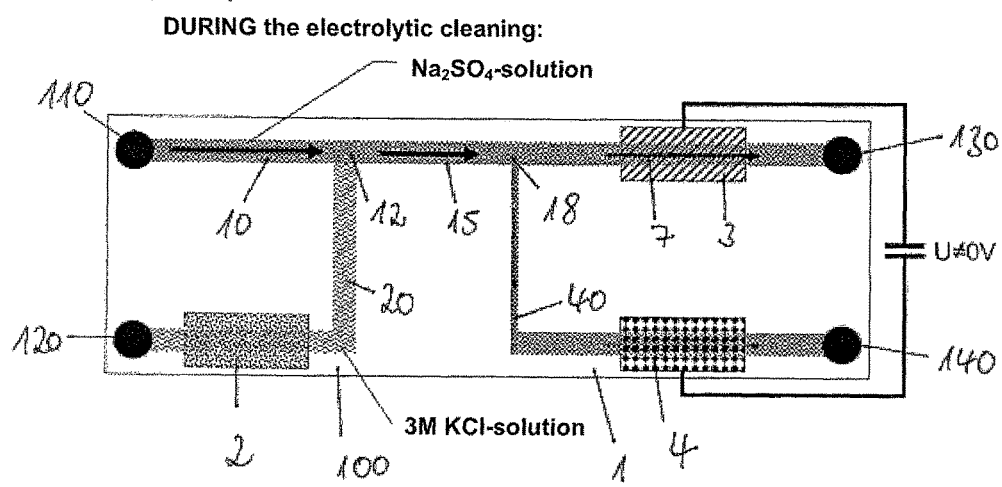
Fig. 4b) DURING the electrolytic cleaning:

METHOD FOR DETERMINING AN ANALYTE CONTENT OF A LIQUID SAMPLE BY MEANS OF A BIOANALYZER

TECHNICAL FIELD

The invention relates to a method for determining an analyte content of a liquid sample by means of a bioanalyzer.

BACKGROUND DISCUSSION

Biosensors, which can be subdivided into affinity based and metabolic biosensors, serve for the preferably selective and specific detection, respectively for concentration measurement, of a predetermined analyte contained in a liquid sample to be examined. The large group of heterogeneous biosensors includes, in such case: a receptor layer, which can have a large number of receptors immobilized on a surface, e.g. receptors such as antibodies, haptens, DNA, cells or enzymes; a signal transducer, which outputs a measurement signal correlated with the amount of the analyte bound on the receptor layer; and a signal processing system for amplification and/or additional processing of the measurement signal output by the signal transducer.

The analyte can be a substance to be detected in a liquid sample, for example, a substance such as a protein, a peptide, an antibody, an enzyme or some other substance to be detected in biochemical, biological or medicinal systems. The analyte can, however, also be cells, cell components or DNA or, for example, active ingredients, which are to be detected or determined in the context of environmental monitoring or in the monitoring of water quality.

In the case of affinity based biosensors, it can, in given cases, be necessary to connect to the receptors of the receptor layer, besides the analyte, yet other substances. A substance, which preferably binds with high specificity and selectivity to a receptor, is here generally referred to as the target molecule or also as a ligand for such receptor. Thus, in the case of a given biosensor, the analyte represents a target molecule for the receptors. Other target molecules can, however, also be molecules different from the actual analyte, and these likewise attach to the receptors of the receptor layer, and compete, for example, with the analyte, for binding locations of the receptor layer.

In the case of metabolic biosensors, there is catalytic conversion of the analyte and/or other target molecules after their temporary binding to the receptor layer, which, in the case of metabolic biosensors, contains at least one enzyme, a cell, a cell component or other catalytically effective biomolecule, which can catalytically convert the analyte, in given cases, with additionally present substances.

For detection or for determining concentration of an analyte in a liquid sample, the liquid sample is brought in contact with the receptor layer, so that analyte molecules and, in given cases, other target molecules present in the liquid sample attach to the receptor layer or are converted by the receptor layer. In this way, physical and/or chemical changes are effected, for example, a change of coating thickness, index of refraction, light absorption or electrical charge. These changes can be detected and quantitatively determined by means of the signal transducer. Suitable signal transducers for registering said changes include, for example, optoelectric sensors, and amperometric or potentiometric sensors. The target molecules bound on the receptor layer can also be marked directly or indirectly with a marker, which has, for example, luminescent or magnetic properties, or be marked subsequently directly or indirectly after the binding of the target molecules on the receptor layer. In this case, an optical sensor is suitable as signal transducer for registering the luminescence, or a magnetic sensor for registering magnetic properties. Further suited as markers are also enzymes, which catalyze a following chemical reaction, wherein the course of the reaction can be registered with correspondingly suitable signal transducers.

Numerous different heterogeneous biosensor methods are known. The most frequently used methods will be mentioned and briefly explained by way of example as follows:

Direct method: The analyte binds on receptors of the receptor layer, and no other target molecules are present. In a modification of the method, the analyte is reacted with one or more additional substances (markers) before or after the binding on the receptors, this serving, as a rule, for introducing, directly or indirectly, a physical property, which the analyte does not possess, and so make the binding of the analyte detectable by determining this provided physical property. In the case of the direct method, thus, the binding of the analyte on the receptor layer is directly detected or detected indirectly by detecting the marker reacted with the analyte.

Competitive method: Added to the liquid sample to be examined for an analyte content is, as a rule, a further target molecule (competitor) in known concentration or activity and the liquid to be measured so obtained is then applied to the receptor layer. In such case, there is competition between analyte and competitor for binding on the receptors of the receptor layer. The competitor possesses, as a rule, a marker, which, in turn, introduces, directly or indirectly into the system, a physical property, which can be detected. In the case of the competitive method, thus, the binding of the competitor on the receptor layer is directly or indirectly detected by detecting the competitor marker. The original analyte concentration of the liquid sample can then be derived from the measurement signal.

Binding inhibition test: Added to the liquid sample to be examined for an analyte content is a complementary molecule in known concentration or activity, which bonds to the analyte. Subsequently, the so formed, measured liquid is led over the receptor layer, which has receptors, which bind the free complementary molecules, not bonded to the analyte. This binding can be detected directly by means of suitable methods. Alternatively, the complementary molecules can be reacted directly or indirectly with a marker before or after the binding on the receptors or before or after the bonding to the analyte. In the case of a binding inhibition test, thus the binding of the complementary molecules on the receptors is detected directly or the markers on the complementary molecules are detected directly or indirectly. Then, the analyte concentration of the liquid sample can be derived from the measurement signal.

For preparing the receptor layer, the receptors are immobilized on solid carrier materials, i.e. bound to these. This can occur, for example, by unspecific adsorption of the receptors on the surface of the carrier material, the so called substrate. However, also covalent bonding of the receptors or bonding via a number of other bonding layers are established methods for preparation of receptor layers. Thus, for example, streptavidin can be bonded covalently on a solid carrier surface and, for preparing the receptor layer, biotin-conjugated antibodies connected on the streptavidin binding layer using the affinity interaction between biotin and streptavidin. In general, one speaks of the total layer system constructed on the surface of a solid carrier material as the 'sensor matrix' of the biosensor, wherein the last layer is the receptor layer.

The sensor matrix with the receptor layer is, in many applications, applied on a biochip integrated in a microfluidics system. These biochips are, as a rule, single-use products, which are discarded, respectively replaced by a new biochip, after a single performed determination or concentration measurement of the analyte. Also, in the case of metabolic biosensors, the chip, or the cartridge, which contains the sensor matrix, must be replaced at regular intervals. The reason for this is, generally, the low stability and robustness of biological receptors as well as the often high affinity, with which target molecules are bound on the receptors. Thus, coupled with conditions, under which target molecules bound on the receptors are shed from the receptors is, as a rule, also a more or less large destruction of the receptor layer. Known from the relevant technical literature are only few special cases, in which there is described such a regeneration of the receptor layer, i.e. the almost complete removal of the target molecules while retaining the essentially unchanged functionality of the receptor layer. According to the state of the art, this is, however, not possible for the large majority of biosensors, especially for biosensors for determining proteins.

Automated or semi-automated bioanalyzers, in which single-use chips carrying a receptor layer are used, are known. Thus in European Patent EP 1 343 011 B1, for example, an apparatus is described for electrochemical detection of a nucleotide sequence. This apparatus has a replaceable analytical cassette, preferably embodied as a single use-component, for introducing the liquid sample. The cassette has a measuring electrode with a receptor layer, on which the nucleotide sequence selectively and specifically binds. The analytical cassette is connectable with a calculation system via an analog interface, wherein an electrochemical detection of the nucleotide sequence is performable by means of the calculation system.

For application of biosensors, especially of affinity based biosensors, in process measurements technology, for example, for automated monitoring of a biotechnological process in an industrial plant or for automated monitoring of water, for example, for residues of medicines or for the content of endocrinally active substances, it is, in contrast, desirable, to be able to perform a plurality of measurements one after the other, without requiring for each measurement a replacement or an exchanging of a chip or other component containing the sensor matrix. A possible application of biosensors for such measuring tasks can be a bioanalyzer, which is fed, especially online, liquid samples of a process medium to be monitored. Optionally, the liquid samples can be pretreated, preferably automatically, with reagents, for example, with other target molecules, markers, etc. for performing the above described methods. The bioanalyzer includes furthermore: a receptor layer, to which the liquid sample, or the liquid to be measured, as obtained by pretreating, is fed; a signal transducer, which outputs a measurement signal correlated with the number of analyte, or target, molecules bound on the receptor layer; and a signal processing system, which further processes the measurement signal and outputs a measured value, especially one derived from the measurement signal. The supplying of the samples and, in given cases, reagents to the receptor layer and the draining of the liquid sample, or liquid to be measured, after transpired measuring, can be performed in an automated or semi-automated analyzer by means of pump apparatuses, pneumatic systems or other liquid transport systems. In order to keep the required reagent amount and therewith, also the liquid volume to be disposed after transpired analysis, small, supply and drain lines for the sample and, in given cases, reagents should have cross sections, which are as small as possible, e.g. in the sub-mm range. Such liquid lines with cross sections in the sub-mm range are referred to in the following also as microfluidic ducts. A module of a bioanalyzer, which has such microfluidic ducts, is also referred to as a microfluidic unit.

In order to minimize the maintenance effort for a bioanalyzer used for such purposes, or in order to increase the degree of automation, there is a need for biosensors suitable for performing a plurality of measurements one after the other, wherein the sensor matrix, respectively its receptor layer, is essentially completely regeneratable, or renewable, in situ, with high reproducibility.

Known from the literature are different approaches concerning how sensor matrices or receptor layers of biosensors can be regenerated. Frequently, in such case, the solvent is altered, in order to bring about a releasing of the binding between receptor and target molecule. Frequently for this, the pH-value of the solution is changed. Also, changes of ionic strength or solvent polarity or the addition of specifically acting substances are often applied, in order to achieve a regeneration of receptor layers. Disadvantageous in these methods is, however, that, in order to enable a multiple regeneration of the receptor layer, for each receptor-target molecule interaction, the optimal compromise between optimum regeneration efficiency and minimum destruction of the receptors must be ascertained in complex test runs. A renewing of the receptors, or the receptor layer, is not possible according to these methods.

A. T. Tüdös, E. R. Lucas-van-den Bos, E. C. A. Stigter, "Rapid surface plasmon resonance-based inhibition assay of deoxynivalenol", Journal of Agricultural and Food Chemistry 51 (2003), 5843-5848, describe such a regeneration method for a receptor layer with haptens as receptors that are especially small and robust. Between 499 and 717 regeneration cycles are claimed. For an immunoassay, in the case of which the receptors are proteins, no receptor layers are known, which can be multiply regenerated with similar success.

Known from European Patent EP 2 189 793 A1 is that, for removing the target molecules from the receptors of the respective receptor layer, enzymes can be applied, which selectively decompose the target molecules connected to the receptors. In such case, it must be heeded, however, that the used enzymes do not equally attack the receptors, and this strongly constrains the ability to apply this technique. Due to the chemical nature of such enzymatic decomposition of the bound target molecules, maintaining the same receptor density following multiple performances of the method appears extremely improbable.

A further approach for regeneration of the receptor layer of a biosensor involves binding the receptors via oligonucleotides, thus short DNA, or RNA, molecules. For this, oligonucleotides are covalently bonded to a surface and the receptors or molecules, which form a corresponding binding layer for binding receptors, are conjugated with the complementary oligonucleotide. Specific affine interaction between the complementary oligonucleotides leads to an immobilizing of the receptors on the surface and therewith to the forming of a receptor layer. The affine interaction between the complementary oligonucleotides can be removed chemically or by increasing the temperature, so that the receptors are released from the surface. However, this method in the presence of proteins, e.g. in the presence of antibodies as receptors, is generally not performable, since proteins, as a rule, denature when faced with temperature increase to over 40° C., or in the presence of the reagents needed for the release. In such case, it can come, especially in the case of high protein content, in the case of denaturing the proteins, to the forming of difficultly soluble, protein aggregates, which can only be removed incompletely without aggressive chemical cleaning and which, by the agglutinating and accreting, for example, of liquid lines of the liquid supply- and -drain system, can affect extremely disturbingly the functionality of an automated or semi-automated bioanalyzer. The same is true when the molecules bound on the receptor layer are bridged or cross linked with one another. Also in this case, aggressive chemical conditions must be applied for releasing these bridged or cross linked molecules. In the face of the aggressive chemical conditions, which would be required for removing the protein aggregates, moreover, also the surface bonded oligonucleotides are no longer stable.

Further known from the literature are first approaches for an electrochemical removal of simply structured, biological layers. In contrast to the chemical removal of the sensor matrix, respectively receptor layer, with purely chemical means, e.g. by acids, alkaline solutions or solvents, in the case of the electrochemical removal of the receptor layer, an electrical current flow via the substrate carrying the receptor layer is effected, which leads to oxidative or reductive release (desorption) of the receptor layer, respectively sensor matrix.

Thus, for example, in the articles Seokheun Choi, Junseok Chae "Reusable biosensors via in situ electrochemical surface regeneration in microfluidic applications", Biosensors and Bioelectronics 25 (2009) 527-531, Seokheun Choi, Junseok Chae, "A regenerative biosensing surface in microfluidics using electrochemical desorption of short-chain self-assembled monolayer", Microfluidics and Nanofluidics 7 (2009) 819-827 or Christie A. Canaria et al., "Formation and removal of alkyithiolate self-assembled monolayers on gold in aqueous solutions" Lab on a Chip 6 (2006) 289-295, approaches are described for applying receptors on gold surfaces by means of alkyl thiols as binding molecules, in order, in this way, to provide a receptor layer. Also described in these articles are investigations concerning the problem of how to remove the alkyl thiols used as binding molecules. Problems occur, in such case, especially through re-adsorption of already released alkyl thiols and hydrogen evolution occurring from electrochemical decomposition of the alkyl thiols. Additionally, there is in the case of repeated preparation and removal of the layers a continuous drift observed in the surface occupation, which indicates non-complete removal. In none of the cited article is it explored, whether the cleaning effectiveness is equal in the case of different occupations of the receptor layer. This is, however, indispensable for application in an automated bioanalyzer for process measurements technology, since biosensor measurements are performed, as a rule, based on one or more reference measurements, in the case of which the occupation of the receptor layer occurs, as a rule, either not or almost completely. Especially in the case of SPR measurements, as described in the articles, the quality of the reference measurement is decisively important for the quality of the measurement results. Thus, for example, in the case of Seokheun Choi, Junseok Chae "Reusable biosensors via in situ electrochemical surface regeneration in microfluidic applications", Biosensors and Bioelectronics 25 (2009) 527-531, it is not to be assumed that the cleaning effectiveness is the same in the case of receptor layers, on which much fibrinogen is bound (FIG. 3c), as in the case of receptor layers, on which only little fibrinogen is bound.

For the automated or semi-automated application of the biosensors in process measurements technology, it is important that sequentially executed concentration determinations deliver measurement results comparable with one another. Therefore, a system is needed, which delivers even after a plurality of regenerations, or renewals, of the receptor layer, for example, after 50, 100 or more regeneration- or renewal cycles, for equal target molecule concentrations, essentially equal measurement signals, i.e. measurement signals of comparable intensity, especially in the case of reference of the measurement signals to the reference measurement.

SUMMARY OF THE INVENTION

It is therefore an object of the present invention to provide a method suitable for application in process measurements technology for determining an analyte content in a liquid sample by means of a bioanalyzer of the above described type, respectively to provide a bioanalyzer suitable for performing this method.

This object is achieved by a method for automated in situ determining of an analyte content of a liquid sample by means of a bioanalyzer, which includes a microfluidic system having at least one measurement duct and means for leading one or more liquids through the measurement duct, wherein the measurement duct has at least one substrate, comprising repeatedly performable steps as follows for measuring at least within a measuring region:

(i) preparing a sensor matrix, which has a plurality of receptors, which bind the analyte and/or a further target molecule, preferably selectively and specifically, especially due to an affine interaction, or bring about a chemical conversion of the analyte or of the further target molecule, comprising a step of leading through the measurement duct a preparation solution of at least a first chemical species, which includes at least one functional group binding on the substrate and at least one other functional group, wherein a plurality of the first chemical species are bound on the substrate via the functional group binding on the substrate, wherein the other functional group of the plurality of the first chemical species bound on the substrate serves as a receptor or for subsequent binding of a receptor;

(ii) leading the liquid sample, or a liquid to be measured obtained by treating the liquid sample with at least one reagent, through the measurement duct, wherein analyte contained in the liquid sample or in the liquid to be measured, and/or other target molecules contained in the liquid sample or the liquid to be measured, bind, preferably selectively and specifically, on the receptors or are chemically converted by the receptors, and determining a measured variable correlated with the amount of the target molecules bound or converted by the receptors or with the amount of the analyte bound or converted by the receptors and deriving therefrom the analyte content of the liquid sample; and (iii) regenerating, respectively clearing, the at least one substrate.

The at least one substrate can especially be regenerated, in that the sensor matrix and, in given cases, molecules bound thereto, especially analyte molecules, other target molecules or other substances bound on the sensor matrix, are essentially completely released from the substrate and/or at least partially decomposed. In this way, the at least one substrate can be completely, or essentially completely, cleared, i.e. at least sufficiently cleared that there remain on the substrate residual components of the sensor matrix and possibly substances bound on the sensor matrix only in so little measure that these, in the case of repeating the steps (i)-(iii), i.e. in the case of a new preparing of the sensor matrix, a new leading of a new liquid sample and, in the case of the new regenerating of the substrate, no noticeable influence, especially no noticeable influence on the accuracy of measurement, is exerted.

The sequence of steps (i)-(iii) is referred to in the following for short also as the "measuring cycle". Since the substrate is regularly regenerated, respectively recleared, by removal of the sensor matrix and molecules possibly bound thereto, and, thereafter, the sensor matrix prepared anew, a replacement of the substrate or other mechanical reaching into a bioanalyzer, especially into its measurement duct, in which the method described is performed, for maintenance purposes, is not necessary. The analysis of the liquid sample can, consequently, be performed completely automatically with a large number of measuring cycles following one after the other. Since the substrate is completely or essentially completely cleared, it is assured that in sequential measuring cycles the sensor matrix has an essentially comparable character, which assures very good comparability of the measuring, respectively analytical, results won in the different measuring cycles.

A measurement, which includes especially the leading of the liquid sample or the liquid to be measured through the measurement duct and the determining of a measured variable correlated with the amount of target molecules bound or converted by the receptors or the amount of analyte bound or converted by the receptors and deriving therefrom the analyte content of the liquid sample according to step (ii), can at least be performed within a predetermined measuring region. The measuring region is a part of the surface of the measurement duct. The substrate is arranged at least partially in the measuring region, it can, however, also extend beyond the measuring region within the measurement duct or within other liquid ducts of the microfluidics system.

With the method of the invention, the receptors, on which the target molecules, especially the analyte, are bound, are bound on the substrate via the first chemical species. In such case, the receptor can be formed by the other functional group of the first chemical species. In this case, the receptor layer is formed in a single preparation step by immobilizing the first chemical species on the substrate. The sensor matrix is composed then only of the receptor layer. If the receptor in the form of a functional group is not a direct component of the first chemical species, the other functional group can serve for binding the receptor. In this case, the binding of the first chemical species on the substrate forms a first binding layer, on which, in turn, for example, by specific binding on the other functional group, the receptor can be directly bound or bound via one or more other binding layers. The one or more additional binding layers can be formed sequentially by passing through, in each case, an additional preparation solution, which contains other chemical species binding on the, in each case, uppermost binding layer for forming an additional binding layer. In this way, a sensor matrix is formed of one or more binding layers and a terminating, receptor layer bound on the uppermost binding layer. The lowest binding layer formed by the first chemical species and each other of the binding layers are bound on binding locations of the chemical species forming the, in each case, layer lying therebeneath, preferably through specific affine interaction, e.g. via a biotin-streptavidin binding or the binding between an antibody and its antigen. Also, the receptor is preferably bound via a specific affine interaction on the uppermost binding layer. The application of additional binding layers, i.e. the indirect binding of the receptor on the first chemical species via second and possibly other chemical species offers the advantage that these can be so embodied that, on a given binding layer system, numerous different receptors can be prepared as receptor layer, wherein, however, all receptors use the same functionality relative to their binding, so that there is no need of matching binding layers and receptors.

Step (ii), which includes the leading and analyzing of the liquid sample, or of the liquid to be measured produced by treating, e.g. mixing, the liquid sample with a reagent, can be repeated one or more times, before, in step (iii), a regeneration of the substrate occurs.

Through repeated performing of the sequence of method steps (i) to (iii), the receptor layer, respectively the sensor matrix, can always be reconstructed anew on the same substrate in situ, i.e. without mechanical reaching into the measurement duct, and so, repeatedly, the analyte content of liquid samples supplied the bioanalyzer one after the other can be ascertained in automated fashion. Preferably, the method steps (i) to (iii) can be performed at least 50 times, preferably at least 150 times, further preferably at least 300 times.

The terminology, functional groups, means, generally, atom groups, which decisively determine the material-properties and the reaction behavior of the compounds carrying them. The concept of the functional group includes here and in the following also: atom groups or molecule regions, which can form binding, preferably specific, interactions with other chemical species; as well as also markers bound on a chemical species, especially a molecule, for example, markers formed of molecules, peptides, proteins or protein tags. For example, a biotin molecule bound on an alkyl thiol and serving as binding partner for a receptor-target molecule binding, forms a first functional group of the alkyl thiol. The thiol group of the alkyl thiol forms a second functional group.

The functional group of the first chemical species that binds on the substrate is preferably matched to the substrate material. The substrate can be, for example, of metal or can comprise at least one metal coating.

The term, receptor, means here a functional group as above defined, on which a complementary molecule, also referred to as target molecule, binds, preferably selectively and specifically, especially due to an affine interaction, or by which the conversion of other chemical species is enzymatically catalyzed. In such case, it need not necessarily concern a receptor in the biological sense, such as, for example, an antibody.

A number of different methods are available for determining the analyte content of a liquid sample. For example, the analyte can be bound as a target molecule directly on the receptor layer (direct method). It is also possible to bind on the receptor layer the analyte and a target molecule different from the analyte, in order to register a measured variable correlated with the number of target molecules bound on the receptor layer and to ascertain therefrom the analyte concentration (competitive method). It is furthermore possible to mix the liquid to be measured with a pretreatment solution before the leading through the measurement duct, wherein the pretreatment solution contains a reaction partner of the analyte in a known concentration, and then to lead the mixture through the measurement duct. In this case, the remaining reaction partner not bound to analyte molecules serves as target molecule, wherein, from the number of target molecules bound on the receptor surface, the concentration of the analyte in the measured solution can be deduced (binding inhibition test).

The terminology, determining an analyte content, means a purely qualitative detection of an analyte, a semi-quantitative determining of the analyte fraction in a certain sample volume of the liquid to be measured or even a quantitative concentration ascertainment or activity determination for the analyte in the liquid to be measured.

Preferably, the determining of the analyte content according to the method described here and in the following is not used for determining deoxyribonucleic acid (DNA) and ribonucleic acid (RNA).

The terminology, chemical species, means here and in the following especially a molecule, a complex, a biomolecule aggregate or a microorganism. The molecules can include, for example, enzymes, peptides, proteins or DNA. Examples of complexes are protein complexes, which are also referred to as protein aggregates. Microorganisms can include, especially, cells, such as e.g. yeast cells.

In an advantageous embodiment, the substrate is electrically conductive. It can, in such case, be, for example, an electrically conductive surface region of the measurement duct, which is embodied e.g. as a metal film on a wall of the measurement duct. The substrate can comprise, for example, a chemically stable metal with high thiophilic properties, especially a metal such as gold or platinum. In this case, the functional group binding on the substrate can comprise a sulfur atom bonding, especially covalently, to the substrate. Especially suitable for this are thiol, or disulfide, groups.

Examples of the first chemical species include thiols, especially alkyl thiols and polyethelene glycol thiols. Such molecules are known to those skilled in the art as binding molecules, so-called linkers, for biochemical molecules, especially for receptors of a biosensor (compare the above cited article). With a thiol groups binding surface as substrate, alkyl thiols form covalent bonds between the substrate, for example, a gold, or platinum, substrate, and the sulfur atom of the thiol group and form on the surface frequently self organized monolayers, also referred to as self-assembled monolayers, or SAMs, for short. The forming of such SAMs is, however, not absolutely required for the construction of a sensor matrix, respectively, receptor layer.

The method described here and in the following occurs preferably automatically, wherein a control unit, which includes an electronic data processing unit, e.g. a microcomputer, controls the leading of the liquids through the measurement duct and the registering of measured values. The means for leading the liquids can comprise especially pumps, e.g. syringe pumps, or pneumatic means. The measurement signals output from a signal transducer of the bioanalyzer suitable for registering the measured variable can be converted by the control unit into a digital signal and a measured value of the measured variable can be formed therefrom.

The regenerating of the substrate can occur using purely chemical means, e.g. by leading sodium hydroxide solution containing peroxide through the measurement duct for dissolving the sensor matrix.

The regenerating, respectively the clearing, of the substrate can also occur by producing an electrical current flow between the substrate and a counter electrode in electrically conductive contact with the substrate via an electrolyte, in order to clear the substrate, especially essentially independently of the present occupation of the substrate by the sensor matrix and, in given cases, other substances bound thereto. For removal of the sensor matrix, thus, an electrical current flow is produced between the substrate and a counter electrode, in order to effect a clearing of the substrate, which means a complete or almost complete removal and/or an at least partial decomposition of the sensor matrix and substances possibly bound thereto.

If one of the species applied for preparing the layers contains more than one binding location for a species of the layer lying therebeneath or for a species, which forms the following layer, then, in the case of a high degree of coverage of the individual layers, covalently or non-covalently bonded junctions can occur at the molecular level, so that a cross linked network is formed. In these cases, a removal of the receptor layer by dissolving the layer structure and a clearing of the substrate with purely chemical means, for example, by acids, oxidizing agents or organic solvents, is frequently not complete or attainable only with damage to the substrate. It has, however, been found that an electrochemical dissolving of the layer structure by producing an electrical current flow between the substrate and a counter electrode in electrically conductive contact via an electrolyte connection with the substrate does lead to an as complete as possible release of the total layer structure with clearing of the substrate. Especially, an as complete as possible clearing of the conductive surface can be achieved, when the electrical current flow produced on the surface is sufficient for electrolytic production of oxygen or hydrogen or alternately of oxygen and hydrogen (electrochemical cleaning). Advantageously, an optimizing of the electrochemical cleaning is such that the release of the sensor matrix and molecules bound thereto or other chemical species occurs with at least partial decomposition of the sensor matrix.

The step of producing an electrical current flow between the substrate and the counter electrode can especially be so performed that hydrogen and/or oxygen is formed on the substrate and/or the counter electrode by electrolysis. In this way, in each case, the cleaning action of the oxidation, respectively reduction, of the receptor layer, respectively the sensor matrix, effected by the electrical current flow and the resulting hydrogen, or oxygen, is amplified still more. In the above cited article of Seokhun Choi et al., in contrast, the oxidative desorption of the layers in the presence of chloride containing solutions, such as, for example, a phosphate, sodium chloride solution, is performed during the cleaning, which excludes the applying of higher potentials and a therewith associated, oxidative decomposition of the sensor matrix, since otherwise the gold chloro complexes formed thereby in the case of positive potentials would lead to a destruction of the gold surface. If, however, the presence of chloride and/or cyanide is avoided, the electrochemical cleaning can be executed both oxidatively as well as also reductively at higher, respectively lower, potentials, and thereby the cleaning effectiveness is further improved. Especially, alternate oxidizing and reducing conditions can be established on the substrate. Preferably, during the electrical current flow, the electrically conductive contact between the substrate and the counter electrode is brought about by an electrolyte, which contains cyanide- and/or halogen ions in concentrations of less than 150 mmol/l, preferred less than 15 mmol/l, further preferably less than 1.5 mmol/l, especially when the substrate involves a gold, or platinum, film.

Thus, in the case of a method embodiment, in the case of which hydrogen and/or oxygen is formed on the substrate by electrolysis, a very high cleaning effectiveness can be achieved, which remains equal over more than 50 measuring cycles, and, in each case, subsequently the sensor matrix is reconstructed anew, in situ, with high reproducibility. In internal investigations, it was shown that both a bridged protein layer structure composed of the layer sequence alkyl thiol-PEG-biotin-NeutrAvidin as well as also a highly cross linked protein layer structure composed of the layer sequence alkyl thiol-PEG-biotin-NeutrAvidin-BSA-biotin-NeutrAvidin-BSA-biotin-NeutrAvidin, could, in such case, repeatedly and in equal measure be removed and the, in each case, after the removal of the layer structure, subsequently embodied sensor matrix had the same properties as a sensor matrix, which was constructed in a comparison experiment on a new, non-regenerated substrate.

The counter electrode can be arranged lying within the measurement duct, especially opposite the substrate. Thus, the counter electrode can be, for example, of a chemically very inert material and is preferably applied in the form of a film. Such an inert electrode material is formed, for example, by a layer of boron-doped, diamond-like carbon. Such electrodes are used, for example, in water treatment, and are applied there for electrolytically generating hydroxyl radicals for decomposing organic residues.

The counter electrode can likewise be embodied in the measurement duct, especially lying opposite the substrate, as a further substrate, on which the functional group of the first chemical species binding on the substrate binds. For example, both the substrate as well as also the counter electrode can comprise an electrically conductive material binding thiol groups or disulfide groups. The substrate and the counter electrode serving as further substrate can be formed, for example, as gold or platinum films on oppositely lying walls of the measurement duct. In performing step (i), there is, in this way, formed both on the substrate as well as also on the counter electrode a sensor matrix having a large number of receptors. In performing step (ii), analyte and/or other target molecules contained in the liquid sample or in the liquid to be measured are preferably selectively and specifically bound on the receptors of the sensor matrix formed on the substrate and on those of the additional substrate, or chemically converted by these. A measured variable correlated with the amount of the analyte bound or converted by the receptors of the two sensor matrices or with the amount of the target molecules bound by the receptors of the two sensor matrices can be determined. This is especially advantageous, since the effectively available substrate surface is enlarged thereby, which, because of the correspondingly greater measurement signal, affects the accuracy of measurement positively. The regeneration according to step (iii) serves for clearing both substrates.

For controlling the electrochemical oxidative and/or reductive removal of the sensor matrix, the electrical potential of the substrate can be set, especially controlled, during the producing of an electrical current flow between the substrate and the counter electrode, in reference to an electrical reference potential of a reference electrode in electrolytic contact with the substrate via the electrolyte, especially by means of an electrolyte bridge. The control can be done by the control unit of the bioanalyzer. Through application of a reference electrode for adjusting, or controlling, the potential of the substrate, respectively the counter electrode, the occurrence of too large positive or negative potentials on the substrate connected as working electrode and/or on the counter electrode can be prevented, since otherwise the substrate, respectively the counter electrode, could be attacked or even destroyed. The terminology, electrolytic contact, means an ion conducting contact via an electrolyte, especially an ion containing, aqueous solution. Preferably, a diaphragmless, electrolyte bridge is involved.

In the above cited article of Seokheun Choi et al., there is, in contrast, a reductive removal of a receptor layer by means of a two electrode circuit. Since a reference electrode is absent, there can be no checking of the potentials actually resulting on both electrodes. In this way, it can, depending on the conditions reigning in the microfluidic system and on the electrolyte concentration and -composition, come to too large positive or negative potentials on the substrate or on the counter electrode. These large potentials, when they occur repeatedly, can lead to the destruction of the electrode functionality. This defeats, however, the object of the invention disclosed here.

The reference electrode can be embodied as an electrically conductive coating of an additional liquid duct connected with the measurement duct. It is also possible to use, as reference electrode, a currentlessly operated, pseudo reference electrode in the form of a metal wire, especially a platinum- or gold wire, which can be arranged in the measurement duct or in an additional liquid duct connected with the measurement duct. Should in the course of a measurement cycle it come to an occupation of the pseudo reference electrode by the used reagents, then the pseudo reference electrode is likewise regenerated, or cleared.

With reference to the reference potential of the reference electrode, the potential of the substrate serving as working electrode can continuously or discontinuously, especially linearly, be varied between a minimum- and a maximum value, in order to reclear the substrate by electrochemical cleaning, especially with oxygen-, respectively hydrogen, evolution. Preferably, the potential is moved back and forth, especially linearly, multiple times, especially between 2 and 1000 times, between the maximum- and the minimum values. Likewise, the process duration as well as also the cleaning duration can be variable within broad limits and changed, or set, depending on the cleaning result. For this, the control unit of the bioanalyzer can provide a corresponding input facility for a service person or means for loading predetermined process parameters. Optionally, during or after producing the electrical current flow or interposed therein, the electrical current level occurring on the substrate can be registered, in order so to obtain one or more cyclic voltammograms, from which the state of the electrically conductive surface section can be deduced. Also, alternative analytical methods, for example, optical, voltammetric or other electrochemical analytical methods, can be applied for evaluating the state of the substrate.

Alternatively, also the electrical current level of the electrical current flow produced between the substrate and the counter electrode can be varied continuously or discontinuously between a minimum- and a maximum value, in order to reclear the substrate by electrochemical cleaning. In such case, the electrical potential difference established between the substrate and the reference electrode must not subceed a minimum value, nor exceed a maximum value, in order to avoid damaging the substrate.

If the counter electrode likewise serves as a substrate, then all data and conditions given here for the substrate connected as working electrode hold equally for the counter electrode.

Before, during or after the step of producing an electrical current flow between the substrate and the counter electrode, one or more cleaning- and/or auxiliary liquids can be led through the measurement duct. A cleaning liquid led through before or after producing an electrical current flow between the substrate and the counter electrode serves mainly for chemical cleaning of the substrate. Suitable as cleaning liquids are, for example, acids or alkaline solutions or solvents. Serving as auxiliary liquids are, for example, electrolyte solutions, which support the electrochemical processes on the electrically conductive substrate advantageously (e.g. $Na_2SO_4$ solution or addition of $H_2O_2$). Auxiliary- or cleaning liquids led through the measurement duct during the electrical current flow serve for supporting the electrochemical cleaning. Especially advantageous during the electrical current flow was an acidic, in given cases, supplementally hydrogen peroxide containing, electrolyte solution. The applied electrolyte should not decompose or react at the electrical potentials placed on the electrodes. Here, corresponding so-called conductive salts are known. Acidic phosphate buffers are excellently suited for minimizing currentless decomposition of added peroxides during storage.

Preferably, the electrolyte and/or the auxiliary liquid are/is led during the electrical current flow continuously or discontinuously through the microfluidic measurement duct. In this way, a depletion of needed auxiliary reagents, or an enrichment of reactive, electrolytically produced substances, can be prevented, which has a positive effect on the lifetime of the substrate surface. Furthermore, decomposition products of the sensor matrix and also the gas bubbles formed by electrolysis are removed from the region of the substrate surface, which contributes to a more rapid and safe cleaning.

During production of an electrical current flow between the substrate and the counter electrode, for example, an acidic phosphate buffer solution can be led as auxiliary liquid through the measurement duct. Such an auxiliary liquid is advantageous for supporting an electrochemical cleaning in the case of variation of the potential of a platinum-substrate between negative values in the range between $-0.5$ V and $-1.25$ V (reduction, in given cases, with associated forming of hydrogen) and positive values in the range between $+1.5$ V and $+2.25$ V (oxidation, in given cases, with, associated forming of oxygen) in reference to the potential of a silver/silver chloride reference.

During the regeneration or following the regeneration of the substrate, the substrate can be checked for residual components of the sensor matrix, especially by means of an electrochemical measuring method, e.g. cyclic voltammetry or impedance spectroscopy, an optical measuring method, e.g. ellipsometry, or an adsorption test. Especially advantageously, the electrical current level during the regeneration can be taken into consideration for evaluating and/or for control of the regeneration, respectively regeneration efficiency. In the case of an adsorption test, a substance, which binds on residual components of the sensor matrix on the substrate, is led through the measurement duct and then the amount of the adsorbed substance is ascertained. The checking can also be applied for control of the regeneration.

The auxiliary liquid can include, for example, also photochemically or electrochemically produced ozone, which, because of its strongly oxidizing effect, cares for an effective decomposition of the sensor matrix. Also, other chemical substances or physical methods effective for decomposing the sensor matrix can be used. In such case, can provision of an electrical current flow is not needed, nor then need substrates be electrically conductive.

If, as substrate, a non-electrically conductive, especially non-thiophilic, material is selected and the first chemical species is bound on the substrate in other manner than via a sulfur containing functional group, then a regeneration, respectively clearing, of the substrate can be effected with purely chemical means. For example, the substrate can be glass, on which, with the assistance of a first chemical species, which includes a (trialkoxy)silyl group as first functional group for binding on the glass substrate, the first binding layer for the construction of the sensor matrix is prepared. For regenerating the substrate, respectively removal of the sensor matrix, there can be used, in this case, for example, a solution of 70 vol.-% sulfuric acid and 30 vol.-% hydrogen peroxide solution (30% in water).

Common to all here described methods for clearing the substrate is that there is not merely a release of the analyte bound on the receptors, respectively the analyte molecules or the other target molecules or other substances possibly bound on the receptors of the receptor layer and likewise not merely a release of the sensor matrix from the substrate. Rather, there is preferably simultaneously a decomposition of the components of the sensor matrix and, in given cases, other molecules bound thereby. In this way, a repeated, reliable and secure removal of the sensor matrix is possible largely independently of the complexity of the sensor matrix, especially in the case of a sensor matrix, which has proteins as components and/or in the case of which there is the above described cross linking of the components forming the sensor matrix and/or the molecules bound thereto. Furthermore, all steps needed for a measurement procedure, including the construction of the sensor matrix (step i), determining the analyte content (step ii) and regeneration, respectively removal, of the sensor matrix (step iii) are performed in situ, i.e. by successive leading of corresponding solutions through the measurement duct in a predetermined sequence, without other handling of the measurement duct.

The other functional group of the first chemical species can comprise, for example, biotin. The receptor can, in this case, be bound directly or indirectly via a biotin-binding second chemical species bound on the other functional group of the first chemical species and having at least one biotin-binding location on the other functional group of the first chemical species.

The biotin-binding second chemical species can comprise a biotin-molecule binding, e.g. avidin, an avidin derivative or an avidin-similar molecule, especially streptavidin or NeutrAvidin.

Conversely, also a biotin-molecule binding, e.g. streptavidin, NeutrAvidin or avidin, or an avidin derivative, can serve as the functional group of the first chemical species. The receptor is then bound by means of a biotin group bound on the receptor directly or via a number of binding species, e.g. binding molecules.

The receptor bound on the other functional group of the first chemical species can be bound directly or indirectly on the first chemical species via at least one non-covalent bonding.

When the other functional group of the first chemical species serves as receptor, the layer formed by the first chemical species bound on the substrate is simultaneously a binding, and receptor, layer.

When the other functional group of the first chemical species serves for binding a receptor, the layer formed by the first chemical species forms a binding layer, on which optionally one or more other binding layers can be formed, wherein a receptor layer is provided as terminating layer, which is formed by receptors bound on the therebeneath lying binding locations of the binding layer. The chemical species forming the individual layers can be bound with the chemical species forming the, in each case, thereover or thereunder lying layers by an affine interaction, especially a non-covalent bonding.

Preferably, each layer of the sensor matrix has, relative to the, in each case, layer lying therebeneath, a, with reference to the particular conditions, complete degree of coverage, at least, however, a degree of coverage of more than 80%. In this way, it is assured that measurements with sequentially newly prepared sensor matrices deliver measurement results comparable among one another, since, in this case, always essentially the same number of binding locations is present for the receptors, so that each newly prepared sensor matrix can bind a comparable maximum number of target molecules. This assures a high reproducibility of the measurement signals of the bioanalyzer, in spite of the continuous new preparation of the sensor matrix.

In connection with the present invention, the terminology, "layer" of a sensor matrix is not necessarily to be understood as a morphological description. Rather, the term "layer" refers to the plurality of chemical species bound on chemical species of the layer lying therebeneath or on the substrate in the same binding step and bound in the same way, preferably non-covalently, further preferably via affine interactions. A layer need not only be formed of a plurality of equal chemical species, e.g. equal molecules, especially equal proteins, but, instead, can also comprise a number of different chemical species. Decisive is the binding, via essentially the same physical interactive forces, in the same binding step, e.g. the sending through of a preparation solution comprising the chemical species forming the layer.

For attaining high reproducibility and small individual variations, it is especially advantageous, when the average surface density and advantageously also the average orientation of the receptors of the receptor layer, in the case of repeated or multiple preparing of the sensor matrix, remain as constant as possible. This can be achieved by having the surface density of the individual layers in the case of preparing the sensor matrix be as high as possible and/or as near as possible to the respective equilibrium state composed, respectively, of binding and release of the substance or substances forming the particular layer on the binding locations of the layer lying therebeneath.

The terminology, degree of coverage of more than 80%, means that degree of coverage of a surface, in the case of which the coverage of the surface is greater than 80% of the coverage in the equilibrium state in the case of the conditions used, in each case, for binding, these essentially being the concentration, the flow rate, the binding rate and the geometry of the fluid measurement duct, for the species to be bound from the preparation solution. In the case of a predetermined geometry of the measurement duct, the flow rate and the duration of the leading of the respective solution through the measurement duct can be selected in such a manner and matched to one another and to the concentration of the solution that the degree of coverage of more than 80% is reached. The said parameters can be ascertained in preliminary experiments, and be then provided for performing the described method for ascertaining an analyte content. The degree of coverage can be ascertained by measurements, wherein the degree of coverage of the respective species is measured either directly, for example, by ellipsometry or by means of a quartz microscale, or indirectly by feeding to the respective layer a molecule specifically binding with the respective species, and ascertaining the number of bound molecules, for example, by optical methods.

For reproducible setting of a certain receptor density of the receptor layer, in the case of each layer of the sensor matrix, the particular species forming a binding layer, referred to in the following as the "binding species" or also as the molecule binding, can bind with another chemical species, which binds on the same binding locations of the layer lying therebeneath as the binding species, but which, however, has no other functional group, on which chemical species led subsequently through the measurement duct can bind. The particular surface density of the binding species results from the concentration of the binding species, the concentration ratio and the size ratio of the binding species and the one or more other chemical species as well as the respective equilibrium ratios of binding and release. Analogously, so also can the receptor density of the receptor layer be set. Thus, for example, in the case of a sensor matrix with the layer sequence gold substrate/alkyl thiol-PEG-biotin/ NeutrAvidin/biotin conjugated antibody, mixing in of biotin-polyethelene glycol to the biotin-conjugated antibody can lessen the surface density of the receptors of the receptor layer. In this case, the layer of receptors and polyethelene glycol is likewise referred to as the receptor layer. The density of the binding species in the binding layers can also be set in the same way.

The measured variable correlated with the amount of the target molecules bound by the receptors or target molecules converted by the receptors or correlating with the amount of analyte bound or converted by the receptors can be an optical, measured variable, which is ascertained especially based on a luminescence measurement, a reflection measurement or an absorption measurement. For process suitable bioanalyzers, SPR measurements are less suitable, because of large disturbing influences brought about, above all, by temperature, and electrolyte, fluctuations. For ascertaining the optical measured variable, there can be bound or subsequently bound, for example, on the target molecule, a functional group, which has luminescent properties, i.e. fluorescent, or phosphorescent, properties, or which converts a substrate solution supplied in a following step to produce light (chemiluminescence) or a color change.

When the measured variable is a chemical luminescence brought about directly or indirectly by the target molecule or the luminescence of a luminescent marker of the target molecule, it is advantageous, when the substrate, respectively the measuring region containing the substrate, transmits light in the wavelength range between 300 nm and 900 nm at at least 10%, preferably at least 50%, or even at least 70%. In general, it is advantageous for the application of optical measuring methods in the bioanalyzer, when the measuring radiation is transmitted by the substrate, respectively the measuring region containing the substrate, at at least 10%, preferably at least 50%, or even at least 70%. For example, the substrate can be applied on a wall of the measurement duct as a metal film having a lattice structure. A transmission can, in this case, occur through intermediate spaces of the lattice structure.

In an embodiment, the analyte can be a peptide or a protein, wherein the other target molecule besides the analyte is another molecule different from the analyte, especially a peptide or protein derived from the analyte and having a tag, preferably a protein tag, which serves for direct or indirect production of the measured variable, or which influences the measured variable. The target molecule different from the analyte can be, for example, a competitor, which, due to an affinity interaction, binds, same as the analyte, on the receptor (compare competitive method). Alternatively, the target molecule different from the analyte can be a molecule preferably selectively and specifically binding on the receptor layer, especially a peptide or protein, which forms a complex with the analyte molecules, so that the number of target molecules bound on the receptor layer is a measure for the concentration of the analyte (compare binding inhibition test).

Such a protein or peptide having a protein tag and forming the other target molecule can be produced as a recombinant protein or peptide including the protein tag. Advantageous in such case is that no subsequent chemical coupling of the protein or peptide with the protein tag used for subsequent direct or indirect marking by a marker must occur. If the protein or peptide having the protein tag involves the same basic protein or basic peptide as the analyte, then there is another advantage, namely that the affine interaction of analyte and that of the molecule different from the analyte with the receptors lie, as a rule, often in a similar order of magnitude.

For determining the measured variable correlated with the amount of analyte molecules or other target molecules bound on the receptors, a marker can be bound directly or indirectly on the analyte bound on the sensor matrix or on another target molecule. The marker serves directly or indirectly for introducing a property influencing the measured variable. It can especially be bound via the protein tag on a target molecule having a protein tag. This can be effected, for example, by leading a solution of the marker, or a chemical species carrying the marker as a functional group, through the measurement duct, wherein the marker, or the chemical species carrying the marker, has a functional group binding on the analyte, on the other target molecule or on the protein tag of a target molecule. The marker binds in the latter case specifically on the target molecules bound on the receptor layer and having a protein tag, and not on analyte molecules bound likewise on the receptor layer. Alternatively, it is also an option to mark the target molecules with the marker in a preceding method step, so that target molecules already marked with the marker are led through the measurement duct. The application of protein-tagged, target molecules, preferably as competitors, offers, compared to known methods of protein analysis, the great advantage that, for the determining of different analytes, only a marker, which directly or indirectly binds on the protein tag of the target molecule, is necessary, or the protein tag itself represents the marker. Thus, for example, the application of a green fluorescing protein (GFP) as protein tag acting as marker offers the advantage that this introduces as measured variable its fluorescence, which can be determined directly by means of an optical signal transducer and/or, however, indirectly by subsequent binding of an antibody directed against GFP, for example, an enzyme conjugated antibody.

Suited as directly bound markers are, besides GFP, also other fluorescing substances, such as e.g. fluorescing nanoparticles. Indirectly bound markers can be bound advantageously on a target molecule, or the analyte, via affine interaction. In this case, the described protein tags are especially suitable as universal binding structures for subsequent direct or indirect binding of the marker. Suitable as markers are, besides chemical species, which are detectable, for example, due to certain fluorescent or absorption characteristics, also chemical species, which, in the presence of other chemical species, influence a property of the measuring system detectable, especially optically, by the signal transducer. An example of these are markers, which enter chemical reactions, from which a detectable optical signal arises, especially due to chemiluminescence or a color change. An example of such a marker is peroxidase, which, in the presence of a solution of luminol/H2O2, effects a chemiluminescence catalyzed through the peroxidase.

A bioanalyzer for performing the method of one the above described embodiments includes a microfluidic system having at least one measurement duct and means for leading liquid through the measurement duct, wherein the measurement duct includes at least one substrate, on which, at least within a measuring region, at least at times, a sensor matrix having a plurality of receptors is arranged, which, preferably selectively and specifically, bind or chemically convert target molecules or analyte present in a liquid sample or a liquid to be measured obtained by treating the liquid sample with at least one reagent, wherein the bioanalyzer includes at least one signal transducer, which outputs a measurement signal dependent on an amount of analyte bound on the receptors or converted by these or dependent on target molecules bound on the receptors or an amount of converted target molecules.

The amount of analyte bound, or target molecules bound, corresponds to the number of analyte molecules, or target molecules, bound on the receptors.

Arranged within the microfluidic system can be a counter electrode, which is arranged especially within the measurement duct lying opposite the first substrate and preferably serves as another substrate. If the counter electrode serves as another substrate, then there is arranged also on this other substrate, at least at times, a sensor matrix having a plurality of receptors. The preparing of the sensor matrix and the regeneration of the substrate and the counter electrode serving as another substrate can occur, as above described in connection with the method for automated in situ determining of an analyte content of a liquid sample.

The substrate and the counter electrode can be arranged relative to the flow direction of the electrolyte flowing through the measurement duct in such a manner that gas bubbles occurring in the electrolyte due to an electrical current flow between the substrate and the counter electrode are so led that they essentially do not influence the electrical current flow. The counter electrode can be embodied as an electrically conductive coating of a duct of the microfluidics system, respectively as a film, which especially can be different from the measurement duct, but bonded therewith. It can preferably be arranged within the measurement duct, for example, lying opposite to the substrate or coaxially therewith.

The bioanalyzer can furthermore comprise, formed within the microfluidics system, a reference electrode, which is in electrically conductive connection with at least one substrate via an electrolyte bridge, especially a diaphragm-less electrolyte bridge. The substrate, the counter electrode and, in given cases, the reference electrode can be embodied as electrically conductive, connectable films, especially as metal coatings on the walls of the ducts of the microfluidics system, in which they are arranged.

The microfluidic system can comprise a first component, which has a surface, in which the measurement duct and, in given cases, other ducts, especially ducts connected with the measurement duct for liquid transport, are embodied as depressions, wherein at least a second component is connected with the first component and covers the depressions and liquid tightly seals them relative to the environment. The so formed liquid lines extend between one or more liquid reservoirs, from which liquids can be introduced into the microfluidics system, and waste containers, into the liquids can be transferred from the microfluidic unit. The first and second components can be composed especially of an electrically insulating, preferably transparent, material, e.g. glass or a synthetic material, e.g. a plastic.

The substrate, the counter electrode and, in given cases, the reference electrode can be formed on the second component as electrically conductive, connectable films, especially as metal coatings.

The microfluidic system can, in an alternative embodiment, comprise a first component, especially a planparallel first plate, and a second component, especially a planparallel second plate, arranged spaced from the first component, wherein the first and second components are connected with one another via one or more spacing elements arranged between the first and second components, especially one or more intermediate plates, wherein the one or more spacing elements have intermediate spaces and/or perforations, which form a duct structure extending between the first and second components, including the measurement duct and, in given cases, additional ducts connected with the measurement duct for liquid transport. The first and second components are especially of an electrically insulating, preferably a transparent material, e.g. glass or a plastic. The one or more intermediate plates can be flexible, for example. Thus, they can be embodied, for example, in the form of silicone mats. The first and second components can be embodied, for example, in the form of glass plates. Advantageous here is the application of microscope slides. The substrate, the counter electrode and, in given cases, the reference electrode can in this embodiment be in the form of electrically conductive, connectable films, especially metal coatings, on the first and/or the second component.

In an additional embodiment, electrically conductive, microfluidic small tubes can be used as substrate, as counter electrode and, in given cases, as reference electrode. Thus, for example, the substrate can be a small gold tube, the counter electrode a small platinum tube and the reference electrode a small silver tube lined internally with silver chloride. Advantages in the case of this type of embodiment lie in the simple electrical and microfluidic connectability of these small tubes. An advantageous variant, in such case, is composed of a measurement duct, whose measuring region is formed of a small tube, which is at least internally electrically conductive, for example, a small tube of platinum, in whose interior is placed, coaxially and without direct contact with the small tube, a wire, which is at least electrically conductive on its surface, e.g. a platinum wire. The small tube can serve, in such case, as substrate and the wire as counter electrode and, in given cases, as another substrate. Also, the reversed functionality represents another option. The small tubes can have a wall in the form of a lattice, wherein the spaces of the lattice are transparent to allow the passage of optical radiation, so that the wire in the interior of the small tube is visible. The coaxial arrangement of substrate and counter electrode permits, because of the small separation between substrate and counter electrode, high current densities, which enable a long service life, even in the case of slight removal of the surface of the substrate and/or the counter electrode during the electrical regeneration, respectively cleaning.

For optical measurements, the measurement duct is preferably so embodied in the region of the measuring region that it transmits light in the wavelength range between 300 nm and 900 nm at least 10%. This is, for example, the case for an embodiment of the substrate as a thin platinum layer, whose thickness amounts to between 2 and 30 nm, or in the case of a structured, for example, lined or lattice structured, opaque substrate applied on a transparent material.

In a preferred embodiment, the microfluidic unit is, or, in given cases, a number of microfluidic units are, arranged together with containers for provisioning reagents, respectively reagent solutions, and for accommodating liquid wastes, in a replaceable unit of the bioanalyzer, a so-called replaceable cassette. The containers are connected within the replaceable cassette by means of microfluidic connecting systems with the one or more microfluidic units for supplying the reagents into the microfluidic unit or units, and for draining consumed liquids into the waste containers. Transport of the liquids through a microfluidic unit occurs preferably indirectly, e.g. pneumatically, so that, besides a line for delivery of the liquid sample to be analyzed, no additional liquid conveying lines need to connect to the replaceable cassette. This enables a simple and user friendly operation of the bioanalyzer. After insertion of such a replaceable cassette, filled with the required reagents, respectively reagent solutions, into the bioanalyzer, in an initial step, the fluid lines and ducts are filled with liquid. Hereafter, in situ and directly one after the other, steps i to iii can be executed repeatedly for performing measurements with the assistance of the bioanalyzer. Liquid samples for analysis can be removed from a process medium to be monitored by means of an automatic sample taking system and fed to the replaceable cassette, respectively to a microfluidic unit contained in the replaceable cassette via a connection of the replaceable cassette to the sample taking system. In this way, with the assistance of this on-line bioanalyzer, fully automated measurements can be performed. After consumption of the reagents, respectively reagent solutions, stored and needed for measurement operation, or after complete filling of the containers for accommodating liquid wastes, the replaceable cassette is to be replaced by a new one or a reconditioned one.

BRIEF DESCRIPTION OF THE DRAWINGS

The invention will now be described in greater detail based on the examples of embodiments illustrated in the drawing, the figures of which show as follows:

FIG. 1 *b*) is a second schematic representation of a receptor layer with bound analyte, and target, molecules;

FIG. 3 is a schematic, longitudinal section of the microfluidic unit of FIG. 2;

FIG. 4 *a*) is a schematic representation of the microfluidic unit of FIG. 2 before an electrochemical cleaning, in plan view;

FIG. 4 *b*) is a schematic representation of the microfluidic unit of FIG. 2 during the electrochemical cleaning, in plan view;

FIG. 5 is a schematic representation of a second embodiment of a microfluidic unit of a bioanalyzer, composed of a composite of a first component, a perforated, intermediate plate forming the duct and a second component, wherein:

FIG. 5 *a*) is a schematic representation of the first component in plan view;

FIG. 5 *b*) is a schematic representation of a perforated, intermediate plate forming ducts, in plan view; and FIG. 5 *c*) is a schematic representation of a second component in plan view;

FIG. 6 is a schematic representation of a third embodiment of a microfluidic unit of a bioanalyzer, wherein:

FIG. 6 *a*) is a schematic longitudinal section taken with the cutting plane C-C of FIG. 6 *b*); and FIG. 6 *b*) is a schematic cross section taken with the cutting plane B-B of FIG. 6 *a*).

DETAILED DISCUSSION IN CONJUNCTION WITH THE DRAWINGS

Figure 1A:
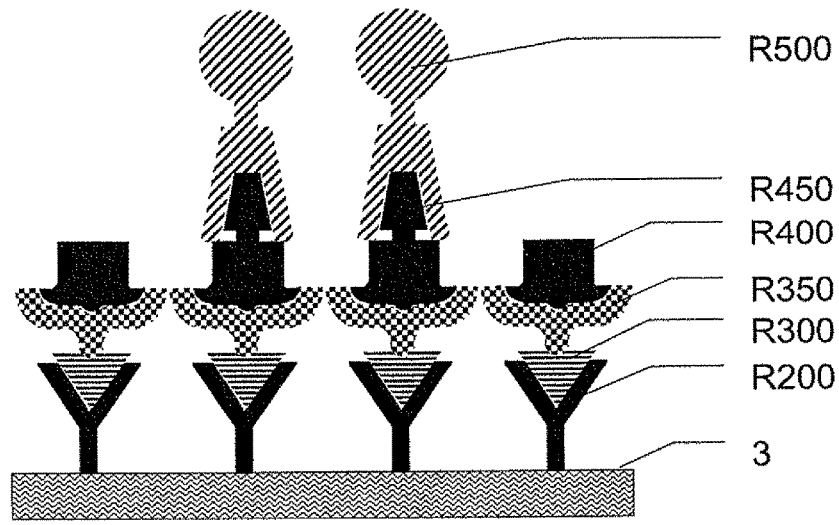
FIG. 1 *a*) is a first schematic representation of a receptor layer with bound analyte, and target, molecules.

FIG. 1*a*) is a schematic representation of a regeneratable sensor matrix of a bioanalyzer with receptors R350 and analyte molecules R400 bound on these and likewise other target molecules R450 bound on the receptors R350. Serving as substrate 3 for the sensor matrix is a thiol groups binding, electrically conductive surface. This can be, for example, a gold, or platinum, surface, which is formed, for example, by a coating, a film or a solid metal piece, e.g. a small tube. Platinum and gold have high thiophilic properties and have, furthermore, the advantage that they are chemically stable, and, in the face of the electrochemical dissolving of the receptor layer and the preparation of a new receptor layer described in detail below, are not changed chemically, especially they do not oxidize.

Arranged on the substrate 3 is a layer of a first chemical species serving as binding molecules R200 for the receptors R350. The binding molecules R200 for forming a binding layer on the substrate 3 can, in the case of a thiophilic surface, such as, for example, a gold or platinum surface, be, for example, alkyl thiols having another functional group, wherein the thiol groups covalently bond with the gold or platinum surface. A further example of binding molecules R200 is α-mercapto ω-biotin polyethelene glycol (referred to, for short, also as thiol PEG biotin). This can be bound from aqueous solution via a metal sulfur binding on the substrate 3. Through optional addition of mercapto polyethelene glycol, which has only one thiol group binding on the substrate 3, not, however, another functional group for binding the receptor R350, it is possible, on the one hand, to set the surface density of biotin groups. On the other hand, the introduced polyethelene glycol prevents the unspecific adsorption of subsequently added proteins on the substrate surface.

The binding molecules R200 have furthermore at least one other functional group, which serves as binding location for the specific binding of a complementary molecule bound via a functional group to the receptor R350. In the present example, the other functional group of the binding molecules R200 is formed by a biotin group of the alkyl thiols. If α-mercapto ω-biotin polyethelene glycol serves as binding molecule R200, then its biotin group serves likewise as functional group for specific direct or indirect binding of the receptor R350. Receptor R350 is in the present example bound preferably selectively and specifically on a molecule R300 binding on the binding molecules R200. Molecule R300 is in the present example a biotin-binding molecule, e.g. streptavidin. Binding molecules R200 and the molecule R300 preferably selectively and specifically binding on the other functional group of the binding molecules R200 and via which the receptor R350 is bound on the binding molecules R200, form a universal interface for binding a large selection of receptors R350 on the same binding molecules R200 and therewith for (indirect) binding of a plurality of different receptors on the substrate 3. The biotin streptavidin connection for binding of the receptor R350 on the binding molecule R200 in the example shown here is well suited as a universal interface, since the biotinylation, respectively the marking of molecules with streptavidin is an established technique in biotechnology. Especially, biotin-functionalized antibodies are widely used, for example, for performing immunoassays.

Bound on the receptors R350 in the example shown in FIG. 1*a*) are analyte molecules R400 and other target molecules R450 competing with the analyte molecules R400 for binding on the receptors R350 and used by the bioanalyzer for detection. The other target molecules R450 are able, like the analyte R400, to bind on the receptors R350, preferably selectively and specifically, by affine interaction. The analyte R400 can be a protein, for example. The protein molecules bind correspondingly, in each case, preferably selectively and specifically, on the receptors R350. In this case, the other target molecules R450 are preferably likewise protein molecules, which bind likewise preferably selectively and specifically, especially by affine interaction, on the receptors R350. Especially, the other target molecules R450 can be marked, or subsequently markable, protein molecules. The other target molecules R450 are provided in the present example with a protein tag. A protein tag is an amino acid sequence bound on the actual protein. Protein tags serve, for example, in affinity chromatography for clean up of a target protein manufactured in a biotechnological method, through specific interaction of the protein tag bound on the target protein with a binding partner used in chromatography columns to isolate the target protein from the remaining products of the method. The protein tag serves in the present example to bind, directly or indirectly, a molecule R500 carrying a marker. The marker possesses physical or chemical properties, based on which the signal transducer of the bioanalyzer can produce a measurement signal, which correlates with the number of the other target molecules R450 bound on the receptors R350 and indirectly with the number of analyte molecules bound on the receptors R350. The marker bearing molecules R500 comprise for this purpose a functional group, which, due to an affine interaction, specifically binds on the target molecules R450, preferably on their protein tag.

If the analyte R400 present in a liquid sample is the protein Pfs, then a corresponding antibody (anti-Pfs) can serve as receptor R350. For determining the analyte content of the liquid sample in a competitive method, a competitor serving as other target molecule R450, in the present case e.g. Pfs (HA-Pfs) recombinantly manufactured and equipped with a hemagglutinin tag (HA tag), is added to the liquid sample and, in this way, a liquid to be measured is obtained for the analysis provided by the bioanalyzer. The molecule R500 carrying the marker can be, for example, an antibody against the HA tag, which is conjugated with a peroxidase. Chemiluminescence effected by means of addition of a solution of luminol/H2O2 catalyzed by the marker peroxidase is converted by an optical signal transducer, which includes especially a photodiode, into an electrical measurement signal, whose signal strength depends on the intensity of the chemiluminescence. This depends, in turn, on the number of marker bearing molecules R500 bound on the target molecules R450. From the measurement signal produced by means of the signal transducer, consequently, the number of target molecules bound on the receptor layer R450 can be deduced and, from that information, the concentration of the analyte molecules R400 in the liquid to be measured can be learned. The measurement signal can be processed by a measurement circuit and/or an electronic data processing unit of the bioanalyzer and, therefrom, the concentration of the analyte in the liquid to be measured, respectively the liquid sample, can be derived.

In order to demonstrate that, with such a universal binding structure constructed of binding molecules R200 and thereon preferably selectively and specifically binding molecules R300 bound on the receptors R350, also completely different immunoassays can be implemented, another example with reference to FIG. 1a) will now be given, in the case of which carbamazepine is to be detected in a liquid sample. As in the previous example, the universal interface for binding of the receptors is formed on the substrate 3 via a large number of biotin groups immobilized by binding molecules R200 and thereto binding Neutravidin or streptavidin molecules R300. On this are bound biotinylated antibodies R350 against the agent, carbamazepine. Thereafter, a liquid to be measured formed from a liquid sample, to which has been added a peroxidase-conjugated carbamazepine derivative, is led over the so formed sensor matrix. The carbamazepine originally contained in the liquid sample binds, in such case, as analyte R400 on the receptors and competes with the peroxidase-conjugated carbamazepine molecules present in known concentration, which, as earlier manufactured conjugates, include both the functionality of the target molecules R450 as well as also the functionality of the molecule R500 carrying the marker. Alternatively, it is also possible to use as competitor carbamazepine bonded covalently to the HA tag. This has, compared with the application of a peroxidase-conjugated carbamazepine derivative, the advantage that the HA tag possesses an essentially smaller molecular weight than the peroxidase, so that the size ratio between analyte and competitor is as small as possible. If analyte and competitor have very different sizes, this can lead to strongly different binding affinities of analyte and competitor, which is frequently undesirable. Especially in the case of low molecular mass analytes such as carbamazepine, a conjugation with such a high molecular mass analyte, as in the case of the enzyme, peroxidase, leads to markedly changed binding affinities, which acts negatively on the lower detection- and determination limit, respectively increases measurement error.

Figure 1B:
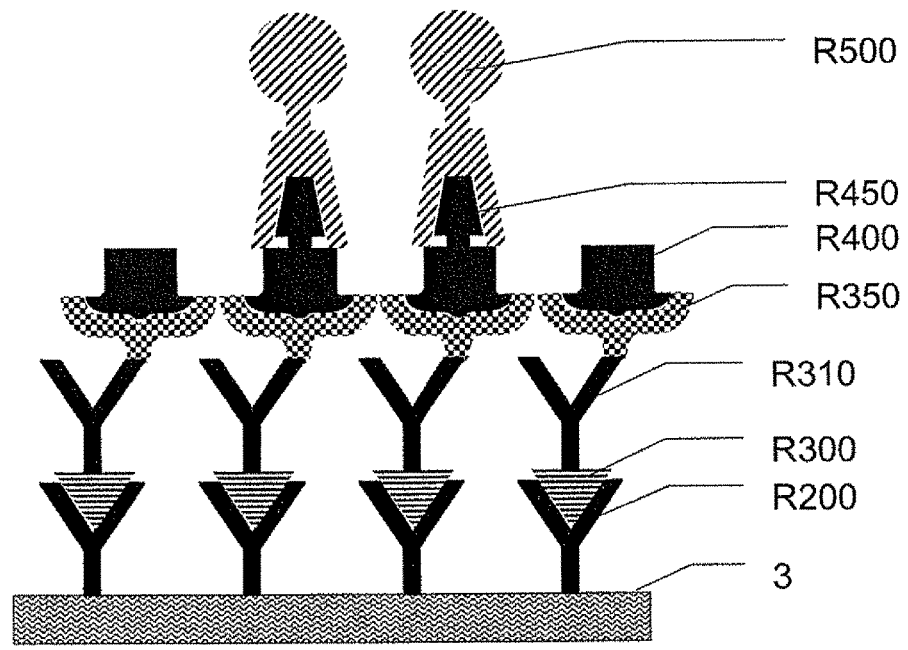

Another universal layer structure for binding receptors R350 is presented in FIG. 1b). Here, the layer structure shown in FIG. 1a) of a substrate 3, a binding layer of a large number of binding molecules R200 and molecules R300 binding preferably selectively and specifically on a functional group of the binding molecules R200 is likewise used for binding the receptors R350. This is, however, supplemented by another binding layer, on which also non-biotinylated receptors R350 can be bound in various ways. This additional binding layer is composed in the example here of a biotinylated immunoglobulin-binding molecule R310, e.g. a biotinylated antibody against immunoglobulins of the type IgG (biotin anti-IgG) or of a biotinylated protein A/G. On this, subsequently, numerous different antibodies well established in past immunologial test methods can be bound as receptors, without having to change the underlying layers or the method for their construction.

Figure 2:
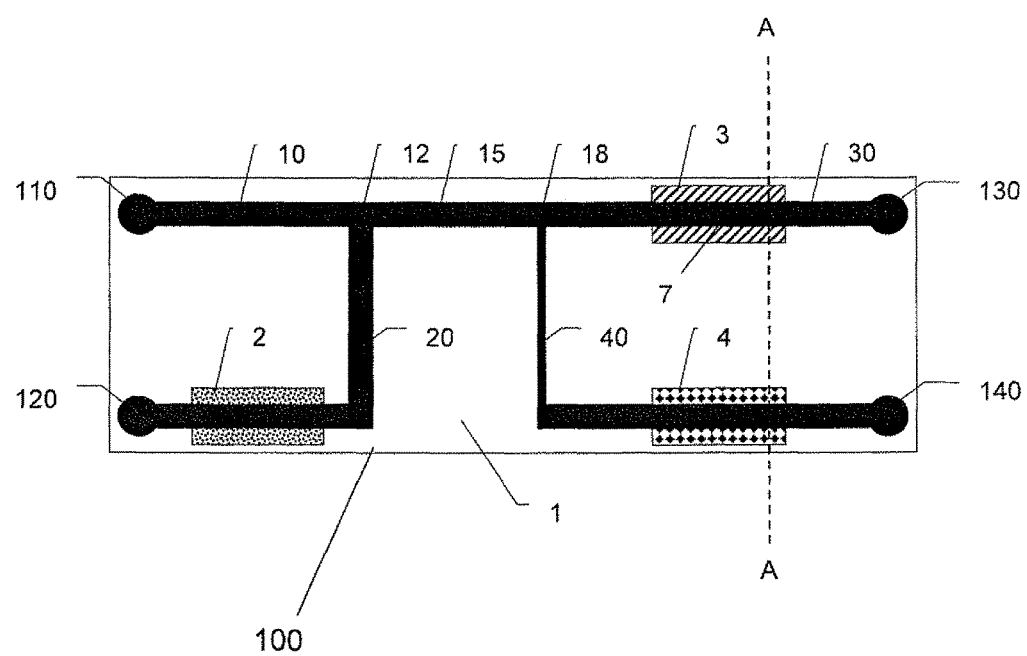
FIG. 2 is a schematic representation of a microfluidic unit of a bioanalyzer in plan view.

FIG. 2 shows in plan view a microfluidic system 100 of a bioanalyzer for detection, or for determining a concentration, of an analyte in a liquid sample. Microfluidic system 100 includes a base 1a, for example, of a transparent synthetic material, which has on a basal plane an open duct structure formed by depressions in the base 1a and including duct sections 10, 15, 20, 30, 40 and junctions 12, 18. Lying on the base 1a and sealing the duct sections 10, 15, 20, 30, 40 relative to one another and against the environment is a terminating cover plate 1b, which is formed, for example, likewise of a transparent synthetic material. This is apparent in the cross sectional view of FIG. 3, as taken on cutting plane A-A of FIG. 2. Platform 1a and cover plate 1b are fixedly connected with one another by a shape, force or material bonded, interlocking connection 1c, for example, an adhesive bonding or a pressed joining. The duct sections 10, 15, 20, 30, 40 sealed by the cover plate 1b form liquid lines, through which are led for performing a measurement the liquid sample to be analyzed and, in given cases, other reagents.

Platform 1a includes, moreover, connections 110, 120 connectable with liquid supplies and connections 130, 140 connectable with liquid drains, through which connections liquids can be fed to the duct structure, or drained therefrom. The supply and drain lines connect the microfluidic system 100 with remotely arranged, liquid reservoirs, in which liquids for performing a measurement, respectively an analysis, are accommodated. Via the supply and drain lines, both the liquid sample to be examined as well as also, in given cases, reagents accommodated in the liquid reservoirs and to be added to the liquid sample are suppliable to the microfludic system 100. The delivery and the draining of the liquids through the duct structure of the microfluidic system 100 can occur, for example, by means of pumps or pneumatically.

Alternatively, the duct structure can, as shown in FIG. 2, also be seen as the basic structure of a microfluidic system, which is independent of the concrete embodiment of the liquid lines. Thus, the illustrated structure can also be constructed, for example, using microfluidic hoses and/or small tubes. The liquid lines have preferably a cross section between $10^7$ and 1 $\mu m^2$, preferably between $10^6$ and $10^2$ $\mu m^2$, further preferably between $10^5$ and $10^4$ $\mu m^2$.

A measurement duct 30 formed by a duct section of the microfludic system 100 includes the substrate 3 already described based on FIG. 1 and embodied as an electrically conductive surface region of the measurement duct. Substrate 3 can be embodied, for example, as a metal film, for example, as gold or platinum film, placed on the cover plate 1b. The region of the substrate coming in contact with liquid flowing in the measurement duct 30 serves as measuring region 7, in which the sensor matrix is constructed and, in given cases, analyte contained in a liquid sample or liquid to be measured led through the measurement duct 30 is bound on the sensor matrix and detected by means of a signal transducer, especially an optical, signal transducer.

A further duct section 40, which is connected with the measurement duct 30 via a junction 18, includes, serving as a counter electrode 4, an additional, electrically conductive, surface region, which is formed, for example, as a metal film placed on the cover plate. Both the substrate 3 as well as also the counter electrode 4 are connected with a voltage source, a potentiostat or a galvanostat, via electrical connections (not shown). If an electrolyte flows through the duct sections 30 and 40, the substrate 3 and the counter electrode 4 are in electrically conductive contact via the electrolyte. By applying a potential difference between substrate 3 and counter electrode 4, an electrical current flow through the electrolyte can be effected.

In the example shown here, in an additional duct section 20, a third electrically conductive surface region is arranged, which can serve optionally as a reference electrode 2. The reference electrode 2 is likewise embodied as a metal layer, especially a silver layer on the cover plate 1b of the microfluidic unit 100 for forming an Ag/AgCl, reference electrode. Here, also, an electrical connection can be connected, for example, to a potentiostat or galvanostat.

A method for preparing the sensor matrix and for detection, or for determining a concentration, of an analyte in a measured solution will now be described with reference to the microfluidic system illustrated in FIG. 2 and a sensor matrix with receptors according to FIG. 1.

First, a sensor matrix is prepared on the substrate 3. The sensor matrix includes a receptor layer with receptors R350, on which bind, preferably selectively and specifically, the target molecules R450 to be determined. In a first step for this, a first preparation solution of binding molecules R200 having a thiol group and another functional group, e.g. alkyl thiols with an additional functional group, is led through the measurement duct 30. The binding molecules R200 bond covalently to the substrate 3 via their thiol groups and form there ideally a monolayer. The preparation solution is led through the measurement duct 30 at a preferably constant flow rate for a predetermined, first length of time, until the degree of coverage of the arising binding layer, as defined above, safely amounts to more than 80%. The length of time required therefor can be determined in preliminary experiments. Such depends especially on the flow rate, the type of binding molecules R200, the concentration of the preparation solution, the binding rate and on additional environmental variables, for example, temperature.

When the forming of the first binding layer of the sensor matrix by the binding molecules R200 has been completed, after one or more washing, rinsing steps (in the following not explicitly stated further), in a second step, a second preparation solution is led through the measurement duct 30. This second preparation solution contains the actual receptors R350, which are bound on a functional group R300 preferably selectively and specifically binding on the first binding layer. For example, the binding molecules R200 forming the first binding layer can have a biotin group, on which a biotin-binding group R300, for example, a streptavidin group, bound on the receptor R350 specifically binds. The feeding of the second preparation solution is performed over a length of time, which is so selected that the degree of coverage of the receptor layer formed by receptors bound on the binding molecules R200 amounts to at least 80%, as above defined. The length of time required therefor can be determined in preliminary experiments.

The preparing of the sensor matrix requires in the present example only two steps, namely binding of the binding molecules R200 on the substrate 3 and the following binding of the receptors R350 via their functional groups R300 on the binding molecules R200. It is, however, also an option that the receptor R350 is not bound on a functional group specifically binding directly on the first binding layer, but, instead, first is bound via one or more other binding molecules, and therewith, via one or more other binding layers, on the first binding layer. The one or more additional binding molecules are bound in one or more additional steps by the leading of corresponding preparation solutions, which contain, in each case, the binding molecule to be bound on functional groups of the last applied layer. In such case, there results a layer structure of the sensor matrix having one or more binding layers and a terminating receptor layer. Preferably, all layers of the sensor matrix have a degree of coverage at least 80%, as already explained above.

If the receptors R350 have been applied on the surface, then the preparing of the sensor matrix has ended and detection of an analyte or the determining of a concentration of the analyte in a liquid sample, or in a liquid to be measured obtained by treating the liquid sample with one or more additional reagents, can be performed.

The individual method steps for determining a concentration of the analyte depend on the method of detection to be executed. For example, the analyte can be bound on the receptor and the binding detected directly or through binding of an additional receptor on the analyte immobilized on a first receptor (sandwich test method). Instead of the analyte, also a target molecule binding competitively on the receptor can be detected, as already described above. The measured solution containing the analyte can also be earlier mixed with an additional solution (reagent), which contains a target molecule binding on the analyte, so that an analyte and target molecule complex is formed. The mixture is then led through the measurement duct and the remaining free target molecules bound on the receptor layer and detected (binding inhibition test). Known to those skilled in the art are a number of other methods for detection, or for determining concentration, of an analyte by binding target molecules on a receptor layer, as initially sketched in brief. All of these methods can be reproduced by corresponding leading of a measured solution, or a measured solution mixed with one or more reagent solutions, through the measurement duct 30 in the bioanalyzer with the microfluidic unit 100 or with the embodiments described below.

In the present example, a competitive test method is performed. In such case, a mixture of the liquid to be measured containing the analyte R400 with a solution, which contains, serving as competitor, other target molecules R450 of known concentration, is led through the measurement duct 30. The target molecules R450 compete with the analyte molecules R400 for binding on the receptors R350. As earlier described, the target molecules R450 are proteins marked with a protein tag and are, except for the tag, essentially identical with the analyte R400.

After the binding of the target molecules, thus of the analyte R400 and the other target molecule R450, on the receptor layer, in an additional step, there is led through the measurement duct 30 a solution, which contains marker bearing molecules R500, which bind specifically on a functional group of the target molecule R450, in the present example, on the protein tag of the target molecule R450. The marker bearing molecule is, in the present example, an anti-HA antibody peroxidase conjugate. Alternatively, the marker bearing molecule can also be indirectly bound. Thus, on the other target molecules R450 containing the protein tag, for example, in a first step, a biotinylated anti-HA antibody can be bound, on which, subsequently, is bound streptavidin marked with a fluorescent dye as marker bearing molecule.

If the marker is a peroxidase, then, in an additional step, a luminol and H2O2 containing solution is led through the measurement duct 30, which leads to emission of luminescent radiation. The emitted radiation is registered by means of a photoelectric signal transducer (not shown), e.g. a photodiode, and converted into an electrical measurement signal. The measurement signal is output by the signal transducer to a measurement circuit, which amplifies and processes the measurement signal, and the processed measurement signal output to a data processing system, for example, a microcomputer. The data processing system derives from the measurement signal, using a furnished evaluation program, a concentration of the analyte in the liquid to be measured and outputs this to a display system and/or, via a data line, to a superordinated unit. The data processing system can be a component of a control unit, which controls the functioning of the bioanalyzer, processes, stores and outputs measurement signals, and processes and executes input commands from a service person or from a superordinated unit for servicing and/or control of the bioanalyzer.

Depending on which test method is used for the detection, or for determining concentration, of the analyte in the liquid sample, or liquid to be measured, different signal transducers can be used for producing a measurement signal correlated with the number of target molecules bound on the receptor layer. For example, instead of chemiluminescence for detecting the target molecules, also a fluorescence can be excited. In this case, radiation for exciting the fluorescence is radiated into the microfluidic unit in the region of the receptor layer and emitted fluorescent radiation registered by means of a photoelectric signal transducer, e.g. a photodiode. Also an absorption measurement can be performed for detecting the target molecules. In all of these cases, it is advantageous to register the measured radiation, i.e., for example, the luminescent or fluorescent radiation, either through the transparent base 1*a* of the microfluidic unit 100 or through the cover plate 1*b* of the microfluidic unit 100 and, in given cases, to send the necessary excitation radiation (for fluorescent or absorption measurements) correspondingly through the transparent base or through the cover plate. For the case, in which radiation is radiated in or registered through the cover plate 1*b*, it is advantageous, when the substrate 3, on which the sensor matrix is applied, is transparent for radiation of the applied wavelength, which, as a rule, lies between 300 and 900 nm. This is achieved by making the conductive coating forming the substrate 3, for example, the gold, or platinum, coating, sufficiently thin. Preferably, this means here a coating thickness of less than 100 nm, preferably between 10 and 50 nm. A gold or platinum layer of this thickness is sufficiently transparent for optical measurements with measuring radiation in the wavelength range between 300 and 900 nm. In order to achieve the required optical transparency in the region of the measuring region, alternatively, the substrate can also be applied as a structured coating, e.g. in the form of a lined or lattice structure with uncoated, and therewith transparent, intermediate spaces. Another variant in the case of the application of an enzyme as marker and a chromophoric enzyme substrate is one wherein the actual measuring region is followed by a transparent region, for example, in front of the exit 130 in the region of the measurement duct 30, so that the absorption of the liquid flowing through the duct can be measured in the transparent region. Besides peroxidases, also phosphatases and other enzymes are widely applied as markers in bioanalysis. Available for these are also numerous, different, enzyme substrates.

After terminating the measuring, in order to perform a next measuring, a regeneration of the receptor layer is done. Since the releasing of the analyte molecules R400, respectively the target molecules R450, or the releasing of the receptors R350 bound via the binding groups R300 on the binding molecules R200 is not completely possible in sufficiently reproducible manner, for this, the entire sensor matrix, including the analyte molecules R400 bound thereon, respectively the target molecules R450, including all additional molecules bound thereon, is released, in order to reclear the substrate 3. Experiments have shown that the binding molecules R200 and the receptors R350 bound via the binding groups R300 form an interlinked covalently or non-covalently, bonded network at the molecular level, which can be completely dissolved only with difficulty, or after a long time, even at increased temperature, by a purely chemical cleaning, in the case of which a cleaning liquid, such as for example, an acid, an oxidizing acid, a lye solution or an organic solvent, is led through the measurement duct 30.

For complete removal of the sensor matrix and the molecules bound thereon, an electrochemical cleaning method has been found to be effective, in the case of which a potential difference is placed between the substrate 3 and the counter electrode 4, while an electrolyte liquid is led both through the measurement duct 30 as well as also through the additional duct section 40. An electrical current flow due to the potential difference effected between the substrate 3 and the counter electrode 4 through the electrolyte liquid leads to dissolution of the sensor matrix, in given cases, covalently or non-covalently cross linked at the molecular level, including the thereon bound, additional molecules.

In the here described embodiment based on FIG. 2, the substrate 3, the counter electrode 4 and the reference electrode 2 are embodied in the form of a three electrode circuit, wherein, by means of a potentiostatic circuit, a potential difference between the reference electrode 2 and the substrate 3 is set and controlled by means of the counter electrode 4.

For clearing the substrate 3, a constant potential difference can be applied, for example, for a predetermined length of time. It has found to be especially protective of the metal coating forming the substrate 3, when the potential difference applied between the substrate and the reference electrode is varied continuously between a maximum value and a minimum value, e.g. by a linear sweep of potential, wherein the maximum value and the minimum value have preferably different signs, so that alternately an oxidizing potential and a reducing potential lies on the substrate 3. The, especially linear, moving of the potential of the substrate 3 relative to the reference electrode from a starting value to the maximum value, thereafter, to the minimum value and then back to the starting value (or, the other way around) is referred to as a "cycle". Preferably for clearing the substrate 3, a number of cycles, for example, 2 to 100 or even up to 1000, are passed through.

The actual conditions selected for the electrochemical cleaning depend, among other things, on the respective compositions of the electrolyte and the sensor matrix, the geometry of the microfluidic system and the arrangement and choice of material of the substrate 3, respectively the counter electrode 4. These are, as a rule, ascertained in preliminary experiments. In such case, the cleaning method is to be optimized such that, on the one hand, a complete removal of the sensor matrix is assured, while, on the other hand, the electrodes are not attacked. It has been found in beginning experiments that in general, an especially good cleaning effectiveness is achieved, when the potential of the substrate is varied linearly between negative values in the range between −0.5 V and −1.25 V and positive values in the range between +1.5 V and +2.25 V relative to an Ag/AgCl-reference electrode, wherein, upon achieving the maximum- and minimum values optionally the potential is held, in each case, fixed for a length of time of some seconds. In this way, the sensor matrix is exposed alternately to oxidizing and reducing conditions and arising hydrogen, respectively oxygen, so that different components of the sensor matrix release oxidatively, respectively reductively, and, especially, decompose. A purely oxidative cleaning is likewise possible; it has, however, been found that, in such case, the substrate can be damaged. Especially advantageous in the stated ranges of potential is that, at the maximum value, respectively the minimum value, in the presence of an aqueous electrolyte, oxygen, respectively hydrogen, evolution occurs. The formed oxygen, respectively hydrogen, contributes, in such case, supportively to the dissolution and decomposition of the sensor matrix components.

There are numerous, different potential, or electrical current, functions that can be used, examples being triangular, sawtooth, sine, rectangular or different pulse, and step, functions. Especially preferred, in such case, are functions, in the case of which the electrical current flow in each period, thus in the case of each sweep of potential, amounts to approximately zero for a certain fraction of the time, further preferably between 10 and 95% with reference to the duration of a period.

In experiments with substrates of platinum, it has been found that, for an oxidative cleaning, the electrical potential of the substrate is preferably set, at least at times, at more than +0.6 V, preferably at more than +1.0 V, relative to the potential of a silver/silver chloride, reference electrode. For a reductive cleaning, the electrical potential of the substrate is preferably, at least at times, set at less than −0.2 V, preferably at less than −0.4 V, relative to the potential of a silver/silver chloride, reference electrode. Due to the small overvoltage for the evolution of hydrogen on platinum under these conditions, sufficient hydrogen is produced for a reductive cleaning. Preferably, the alternation between oxidative and reductive cleaning occurs as a result of a cyclic or periodic movement of the potential. In an especially simple variant for adjusting the electrical potential, a settable, or changeable, voltage source is used, whose outputs are not referenced to ground potential.

Preferably, maximum electrical current density occurring during a sweep of potential, respectively during a cycle, amounts to more than 2 mA/cm$^2$, further preferably to more than 20 mA/cm$^2$, with reference to the area of the substrate within the microfluidic ducts, especially in the measuring region of the substrate. Preferably, positive electrical current charge flowed during a regeneration, respectively clearing, of the substrate amounts to more than +0.2 C/cm$^2$, further preferably more than +2 C/cm$^2$ and negative electrical current charge flowed to less than −0.2 C/cm$^2$, further preferably less than −2 C/cm$^2$, in each case, with reference to the substrate area within the microfluidic ducts, respectively the measuring region. Additionally, preferably the positive charge and negative charge flowed through the substrate in the electrolytic regeneration, respectively clearing, have magnitudes which are essentially equal, or differ by less than 25%.

The electrical current occurring in the case of a linear sweep of potential on the substrate 3 can optionally be registered and evaluated in the form of a cyclic voltammogram. The so measured cyclic voltammograms can especially provide information as to whether residues of the sensor matrix are still bound on the electrically conductive substrate 3. Thus, successful termination of the cleaning phase can be ascertained based on the registered cyclic voltammograms. Also, other voltammetric analytical methods, such as, for example, square wave voltammetry or differential pulse voltammetry are suitable for this as well.

Based on FIGS. 4a) and 4b), an example of such an electrochemical cleaning method for clearing of the substrate 3 by means of the microfluidic system 100 will now be described in detail. Before applying a potential difference between the substrate 3 and the counter electrode 4, first of all, via the connection 120 to a liquid supply line, a 3 M aqueous KCl solution is led into the duct section 20, then further via the junction 12 into the measurement duct 30 and via the junction 18 between the measurement duct 30 and the additional duct section 40 into the additional duct section 40, in which the counter electrode 4 is arranged. The supply of the liquid through the said duct sections occurs by providing a pressure difference between the intake connection 120 and the drain connections 130, 140, while between the intake connection 110 and the drain connections 130, 140 there is no pressure difference.

As soon as the duct section 20, in which the reference electrode 2 is arranged, is filled for the electrochemical cleaning with the KCl solution, a cleaning electrolyte for the electrochemical cleaning, for example, a 100 mM Na$_2$SO$_4$ solution, is led via the supply connection 110, through the measurement duct 30 and via the junction 18 also into the duct section 40 with the counter electrode 4. Found suitable as cleaning electrolyte furthermore is also an acidic phosphate buffer solution (pH=2.1) with 100 mmol/l phosphate content, to which, in given cases, is added 0.25 vol.-% hydrogen peroxide. In general, the composition of the cleaning solution is to be so selected that an as high as possible electrical current flow is enabled at small potentials between substrate and counter electrode. In this way, a high cleaning effectiveness is achieved with little or no damaging of the electrodes.

The leading of the cleaning electrolyte on this flow path is effected by applying a pressure difference between the supply connection 110 and the two drain connections 130, 140. At the same time, it is assured that there is no pressure difference between the second supply connection 120 and the drain connections 130, 140, so that flow of the Na$_2$SO$_4$ solution in the duct section 20 with the reference electrode 2 is prevented. At the junction, there forms, consequently, a transition between the earlier introduced KCl solution and the Na$_2$SO$_4$ solution, via which a charge carrier exchange is possible. In this way, a diaphragmless electrolyte bridge is formed for the reference electrode, whose reference electrolyte, the KCl solution, is, via the junction, in conductive contact with the Na$_2$SO$_4$ solution serving as cleaning electrolyte, without requiring a porous diaphragm, a gap, a fritted glass or other means physically separating the reference electrolyte from the cleaning electrolyte.

After the measurement duct 30 and the duct section 40 with the counter electrode 4 are completely filled with the cleaning electrolyte, a potential difference is applied between the substrate 3 and the counter electrode 4. This can occur, for example, by applying a certain potential to the substrate 3 relative to the reference electrode 2. The liquid junction between the KCl electrolyte contained in the duct section 20 and the cleaning electrolyte accommodated in the duct section 10, 15 at the junction 12 between the duct section 10 and the duct section 20 forms a diaphragmless, electrolyte bridge, via which the reference electrode 2 is connected with the substrate 3. Using the potentiostatic circuit, the electrical current between the substrate 3 and the counter electrode 4 is so set that the desired potential is achieved. Correspondingly, there arises also a potential difference and an electrical current flow between the substrate 3 and the counter electrode 4. As above described, the potential applied to the substrate 3 relative to the reference electrode 2 is moved, for example, linearly, between a maximum- and minimum value multiple times. This procedure has proved to be especially protective of the metal film forming the substrate 3.

Gas bubbles occurring in the electrochemical cleaning of the substrate 3 or the counter electrode 4, in given cases, for example, due to hydrogen or oxygen evolution on one of the electrodes, are drained in the direction of flow (compare the arrows of FIG. 4b)) of the electrolyte liquid from the junction 18 via the drains 130, 140 away from the duct system of the microfluidics system. Equally, also molecules, molecule parts or molecule aggregates released from the substrate 3 are drained from the measurement duct 30 in the direction of flow, so that re-adsorption is prevented.

Figure 5A:
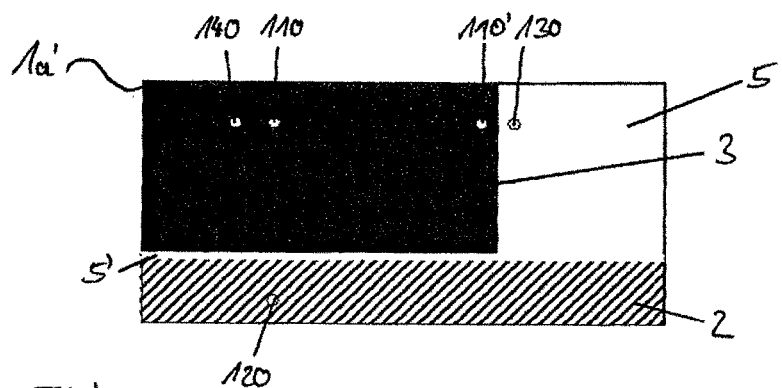
Figure 5B:
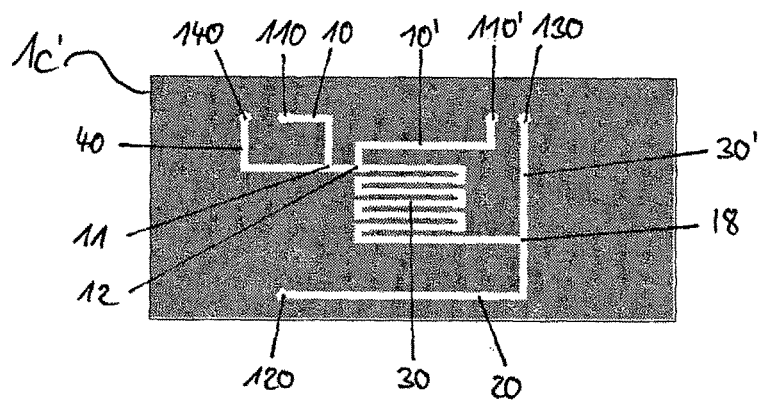
Figure 5C:
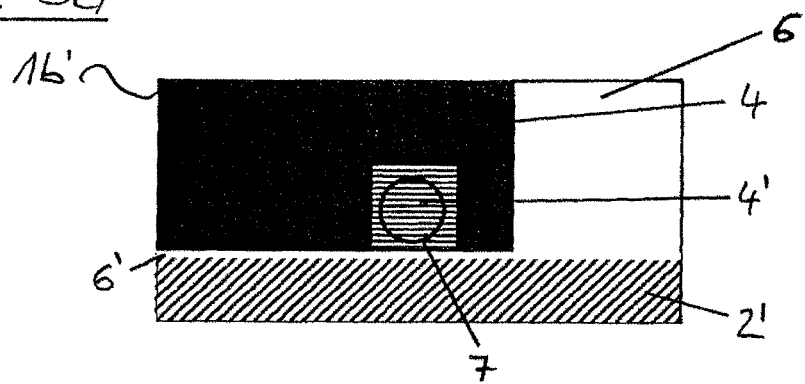

Numerous alternative embodiments of the microfluidic unit of the bioanalyzer are possible. FIG. 5 illustrates a preferred embodiment of a microfluidic unit. Equal components are referenced with equal reference characters as used in the previous example. The microfluidic unit includes a first component 1a' (FIG. 5a)), a second component 1b' (FIG. 5c)) and, arranged between the first component 1a' and the second component 1b', an intermediate plate 1c' (FIG. 5b)), all of which are shown in FIG. 5 in plan view.

The first component 1a' shown in FIG. 5a) can be of a transparent material, for example, glass or a plastic. Visible in plan view are the reference electrode 2 and the substrate 3, which are embodied as films. Serving as reference electrode 2 is e.g. a silver/silver chloride, reference electrode, which was formed of a silver film applied on the component 1a', in given cases, via one or more intermediate layers, especially tackifiers. The surface of the silver film was chlorided, for example, by treating with an iron(III) chloride solution. Substrate 3 is likewise applied as a film on the first component 1a', in given cases, via one or more intermediate layers. In such case, it can be, for example, a 50 to 500 nm thick platinum layer applied e.g. by means of sputtering. The platinum layer serves as a thiophilic substrate for binding a sensor matrix by means of the forming of a platinum sulfur binding of a first chemical species forming a first binding layer. Substrate 3 and the reference electrode 2 are electrically connectable (via connections not shown in greater detail) with e.g. a measurement circuit and/or a voltage source, e.g. a potentiostat or galvanostat.

The regions 5 and 5' of the component 1a' are not coated with an electrically conductive material. In given cases, the regions 5 and 5' can be coated with a chemically stable and electrically insulating material, such as, for example, silicon nitride $Si_3N_4$, in given cases, this being done only in the regions adjoining the electrodes. Preferably, such a coating is applied, for instance, 10 to 100 μm overlapping on the electrode surfaces and so can effectively avoid an underetching of the electrodes, thus, for example, an attacking of a bonding aid, such as titanium dioxide, during the electrochemical clearing of the substrate 3. Further designated with 110, 110' and 120 are the supply connections of the microfluidic unit and with 130 and 140 the drain connections of the microfluidic unit. These are executed in the illustrated example as bores, wherein, on the surface not shown in the view, for example, conventional connectors can be mounted, e.g. by adhesion, for the connection of microfluidic hose lines.

FIG. 5c) shows the second component 1b' of the microfluidic unit in plan view. The second component 1b' can, as the first component 1a', be formed of a transparent material, for example, glass or plastic, wherein electrodes 2', 4 and 4' as well as electrically insulating regions 6, 6' are provided on the second component 1b' in the form of films, in given cases, via intermediate layers, especially bonding promoting, intermediate layers. The reference electrode 2' is embodied equally to the reference electrode 2 applied on the first component 1a'. The counter electrode includes a first counterelectrode region 4 and a second counterelectrode region 4'. The first counterelectrode region 4 is formed of an electrically conductive, chemically inert substance, e.g. boron-doped diamond or platinum, applied in the form of a complete film. In the region 4', which, in the assembled microfluidic unit, lies in the region of the meander shaped measurement duct 30, the counter electrode is embodied in an interrupted manner. In the illustrated example, such is a lined structure connected laterally with the counterelectrode region 4, e.g. constructed of lines of, for instance, 10 μm width, which are arranged in parallel at mutual separations of, for instance, 20 μm. Likewise other dimensions and geometries, for example, a lattice structure, would be applicable here. In the case of application of an optically non-transparent electrode material, there is thereby created in the measuring region 7 of the measurement duct, thus in the region, which is utilized with the assistance of a corresponding signal transducer for obtaining a measurement signal, a partial optical transparency. Thus, in a preferred embodiment of the microfluidic unit of a bioanalyzer, which is operated with an indirect method with the assistance of an enzyme marker, for example, an optical signal transducer is arranged below a region or a portion of the counter electrode 4', whose registration region is formed by the measuring region 7 indicated in FIG. 5c) by the circular area. The signal transducer can have, for example, a photodiode, which registers chemiluminescent light catalytically produced by the enzyme marker and converts such into a proportional electrical current signal. The counter electrode 4, 4' and the reference electrode 2' have connections, not shown in greater detail, for electrical contacting. In the assembled state of the microfluidic unit, the reference electrode 2 formed on the first component 1a' and the reference electrode 2' formed on the second component 1b' can be electrically conductively connected with one another and/or contacted by a shared connection from the measurement circuit, for example, a potentiostat or galvanostat.

The perforated intermediate plate 1c' shown in FIG. 5b comprises, for example, an elastic, 125 μm thick mat of polydimethyl siloxane (PDMS). For forming the microfluidic unit, the base surface of the first component 1a' facing the viewer in FIG. 5a) and the base surface of the second component 1b' facing the viewer in FIG. 5c) are arranged facing one another, spaced from one another and lying opposite one another, and the intermediate plate 1c' is interposed aligned with the components 1a' and 1b' as spacing element between the two components 1a' and 1b'. If the intermediate plate 1c' is formed of an elastic material, the first 1a' and second components 1b' can be connected together liquid tightly by pressing both sides against the intermediate plate 1c' arranged therebetween and so form the microfluidic unit with a duct structure sealed relative to the environment. The width of the ducts amounts in the illustrated example to 500 μm. In an alternative embodiment, the duct forming, perforated intermediate plate is produced in a photolithographic process from a photosensitive material, for example, from a photoresist. Preferably, in this case, the intermediate plate 1c' is fixedly connected with the first and second components 1a', respectively 1b'.

The so formed duct structure will now be described as follows. The reagents, respectively reagent solutions, required for constructing the sensor matrix (step i), performing the measuring (step ii) and regenerating, respectively clearing, the substrate (step iii) can be fed via the connections 110 and 110' from supply containers, or sample feed supplies and, in given cases, mixing systems (not shown). Optionally, the microfluidic unit can also have other connections (not shown). In a preferred variant, the reagents, or reagent solutions, which can interact with one another, are fed to the microfluidic unit via two different supply lines. In this way, it is prevented that such components interact with one another already in the supply system, e.g. that one of the subsequent reagents might interact with an earlier, other reagent sent through the supply line and still remaining adsorbed on the walls of the supplying system. In the case of a longer operation of a bioanalyzer of the invention, such interactions of components and reagents in the supply systems can lead, on the one hand, to greater accreting and, on the other hand, lead to an initial decrease of the concentration of reagents as they move through the microfluidic unit, especially through the measurement duct 30, which, especially in the case of analyses, which require a low limit of detection, negatively affects the reproducibility of the measurement results, respectively can increase the length of time that the reagents must be supplied and, therewith strongly, the consumption of reagents.

The duct section 10' coming from the connection 110' meets at the duct junction 12 the duct section 10 coming from the connection 110. At the duct junction 11, the liquid can be led via the duct section 40 into a waste containment (not shown) connected to the drain connection 140, this corresponding to a bypassing of the measuring region. In such case, the external circuitry of the microfluidic unit leads the flow correspondingly via liquid drive means and valves. An advantage of the bypass formed by the duct section 40 is that the reagents, respectively reagent solutions, can, in this way, first be guided past the actual measuring unit, until initially possibly contained gas bubbles are removed from the supply systems and until, in the case of replacement of a first reagent, respectively first reagent solution, by a second, the resulting reagent, respectively reagent solution, concentration gradient of transition to the second reagent, respectively reagent solution, has passed through the duct system or at least the duct junction 12. By this preparatory leading of the reagents, or reagent solutions, it can be assured that, in the case of the leading of the reagents, or reagent solutions, through the measurement duct 30, which leads through the measuring region, these are passed through from the beginning with the same concentration and essentially free of gas bubbles, such having a positive effect on the reproducibility of the measurement results in the case repeated performing of the above described method steps i to iii with the automated bioanalyzer.

The measurement duct 30 is meander shaped in the present example, wherein preferably all ducts of the microfluidic unit have the same cross section. In this way, gas bubbles, when introduced externally into the microfluidic unit and, above all, those which arise in the case of an electrochemical regeneration, respectively clearing, of the substrate, can very simply and with decreased danger, that they cling on the duct walls in regions with greater duct cross section, be moved back out of the microfluidic unit. The measurement duct 30 meets at the junction 18 an additional duct section 20, through which via the supply connection 120 reagents for assuring a stable reference potential of the reference electrodes 2 and 2', for example, a 3-molar potassium chloride solution, can be fed. The liquids, which are led through the measurement duct 30 and through the duct section 20, flow to the duct junction 18 and then, as controlled by the external circuitry and liquid drive systems and valves, through the duct section 30' and the drain connection 130 into a downstream connected, waste containment (not shown). In this way, a penetration of chloride-ions into the region of the measurement duct 30 is effectively prevented.

As in the earlier described example, the reference electrodes 2, respectively 2', are in electrical contact with the substrate 3 and the counter electrode 4 and 4' via a diaphragmless electrolyte bridge. Also, the gas bubbles arising during the electrochemical regeneration, respectively clearing, of the substrate interrupt this electrical contact between the reference electrode 2, 2' with the substrate 3, connected as working electrode, and the counter electrode 4, 4' only momentarily, when a gas bubble is located at the end of the measurement duct 30, shortly before the duct junction 18. Since the gas bubbles, however, due to the, preferably at least at times applied, volume flow through the measurement duct 30 and the, likewise preferably at least at times applied, volume flow through the duct section 20, are led quickly into the duct section 30', this interruption of the electrical contact between reference and working-, respectively counter electrode is only of short duration and can, moreover, be detected and compensated, for example, with electronic aids.

The microfluidic unit according to FIGS. 5*a*) to *c*) illustrates the geometric relationships between measurement duct, measuring region, substrate and counter electrode. The measurement duct 30 is the region of the microfluidic system, in which the sensor matrix of the bioanalyzer, in the case of the leading through of the reagents required for its construction, is built in always equal and reproducible manner on the therein arranged substrate. In the microfluidic unit according to FIGS. 5*a*) to *c*), this is the duct region 30 up to the end of the substrate, shortly before the duct junction 18. Also, in the duct region between the duct junctions 11 and 12 and in the duct region 40 of the bypass, the preliminary movement of the reagents, respectively reagent solutions, through these duct sections leads to construction of a sensor matrix. This can, however, vary in its composition and density or after the passing through of gas bubbles be even partially or completely without function. The substrate and the counter electrode cover supplementally, besides the measurement duct in the example shown in FIG. 5, also the duct regions 10, 10' and 40 as well as the duct junctions 11 and 12. Also here, other geometries are possible. Necessary for an operation of the microfluidic unit of the invention is that the substrate be present at least partially at least in the measuring region. The measurement duct containing the substrate, on which the complete sensor matrix is constructed in reproducible manner, can, however, also extend supplementally outside of the region 7 registered by the signal transducer. An example of this is the replacement of the photodiode in the example of the microfluidic unit illustrated in FIGS. 5*a*) to *c*) for registering the chemiluminescent signal caused by the enzyme marker with an optical apparatus for measuring transmission, which can be arranged, for example, on both sides of the microfluidic unit and determine transmission at the end of the duct section 30, shortly before the duct junction 18. In the case of the application of a chromophoric instead of a chemiluminescent enzyme substrate, the entire region of the duct section 30 covered by substrate is used and no longer only the region in the registration area of the photodiode as measuring region, since this entire region is utilized for obtaining the measurement signal in this case of a transmission change of the enzyme substrate solution led through the measurement duct 30 and checked with the assistance of a signal transducer connected after the measurement duct.

The substrate 3 connected as working electrode and the counter electrode 4, 4' are so arranged relative to the microfluidic ducts that the duct sections 10, 10', 30 and 40 as well as the duct junctions 11 and 12 are covered by these liquid tightly. In this way, it is assured that in these regions a complete clearing of the substrate surface by electrochemical regeneration, respectively cleaning, occurs. Through the approximately equal separation between substrate and counter electrode throughout all duct regions, the clearing of the substrate surface likewise occurs largely equally throughout all duct regions and without essential differences in the distribution of the electrical current density flowing through the substrate surface. This is advantageous, since, thereby, a surficial release of the substrate occurring, in given cases, due to the regenerating-, or cleaning conditions, affects all regions equally, especially the regions in the measurement duct, and, thus, enables a frequent regeneration and therewith a frequent in situ performing of measurements by means of the bioanalyzer coupled with constant high quality of the measurement results. As already described above, the counter electrode 4 and 4' can also serve as another substrate for the construction of a sensor matrix. In such case, the counter electrode is composed preferably of the same material as the substrate 3, in the illustrated example thus of platinum. Occurring on this other substrate then during the performing of the steps i to iii are preferably essentially the same processes as on the region of the substrate 3 lying opposite in the microfluidic duct.

Figure 6A:
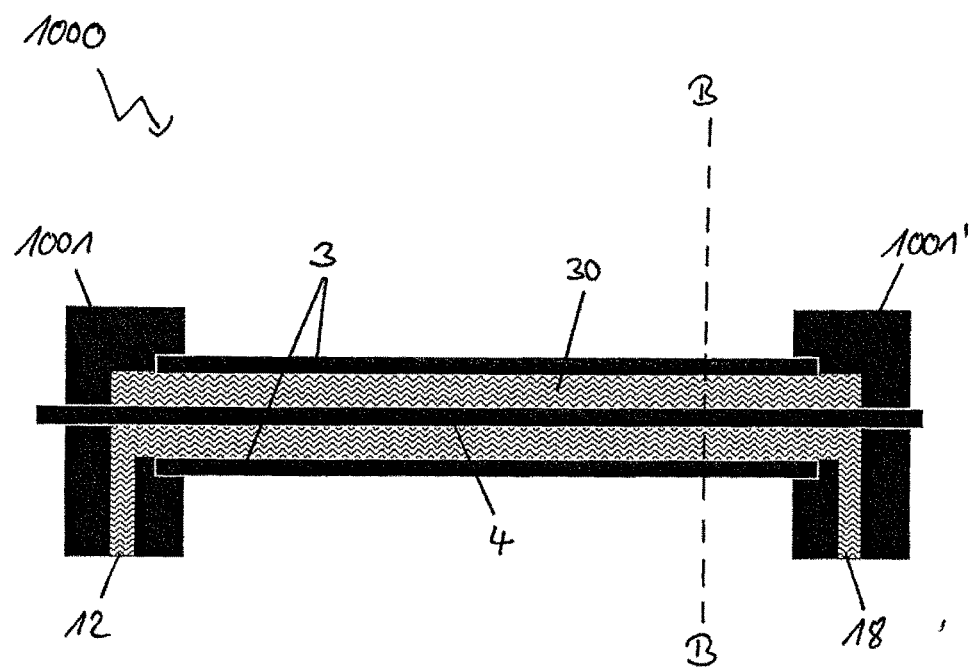
Figure 6B:
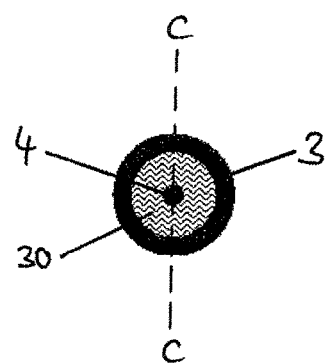

FIG. 6 shows another embodiment in the form of a microfluidic unit 1000. In such case, electrically conductive, microfluidic small tubes, respectively wires, are used as substrate 3 and as counter electrode 4. Thus, the substrate 3 is composed, for example, of a small gold tube and the counter electrode 4 of a gold wire arranged coaxially with the substrate 3. Advantages of this type of embodiment lie in the simple electrical and microfluidic connectability of these small tubes by means of corresponding holders 1001, 1001'. The small tube 3 serves, in such case, as substrate and the wire 4 as counter electrode and likewise as another substrate. Also, the reversed functionality represents another option. The coaxial arrangement of substrate 3 and counter electrode 4 permits through the small separation between substrate and counter electrode high current densities, which enables a long service life also coupled with slight removal of the surface of the substrate and/or the counter electrode in the case of the electrical regeneration, respectively cleaning. Through corresponding connecting by means of microfluidic hoses and small tubes, also more complex microfluidic units, which are constructed not or only partially as microfluidics chips, can be implemented.

After some cycles, in which the potential of the substrate 3 is moved between the maximum and the minimum values, the substrate 3 is essentially completely cleared. Thereafter, a renewed preparation of a sensor matrix in the above described manner can be formed, in order then to be used for a renewed measuring. In this way, at least 50, or even 100 to 200, measurements can be performed with, in each case, a newly prepared sensor matrix.

Since the sensor matrix is regularly prepared completely anew, it is also possible to perform sequential measurements of various analytes, wherein then, in each case, a sensor matrix having certain receptors is prepared, which are suitable specially for the respectively to be determined analyte. For example, in sequential preparations, different, preferably selectively and specifically binding receptors, in each case, for an analyte currently to be detected, or for target molecules applied correspondingly for the analyte detection, can be bound on the binding molecules R200.

In an alternative and preferred construction of the microfluidics system, the counter electrode and the substrate can be arranged within one and the same duct lying opposite one another. In such case, the reference electrode is arranged in a duct connected via a junction with the measurement duct section, so that it is, as shown in FIG. 4*b*, connected conductively with the substrate via a diaphragmless electrolyte bridge during the electrochemical cleaning. When the substrate and the counter electrode are arranged lying opposite one another in the measurement duct, in the case of the above described method for preparing the sensor matrix, a sensor matrix is constructed both on the substrate as well as also on the counter electrode, so that the two can be utilized for generating the measurement signal. In such case, for example, the substrate can be transparent for measuring radiation, so that, for example, luminescent radiation produced on the counter electrode and the substrate is transmitted through the substrate and can be registered as measurement signal by a photodiode arranged behind the substrate.

An important requirement for a bioanalyzer used for monitoring a (quantitative) analyte concentration in an industrial process is the reproducibility of the measurement signals output by the bioanalyzer in the case of sequential measurements with continually interposed, regenerated sensor matrix. Especially, it must be assured that the bioanalyzer, in the case of sequential measurements, between which, in each case, a new preparing of the sensor matrix was performed, in the case of analyte concentration remaining equal, in fact outputs a measurement signal of the same signal strength.

In order to assure this with the method described here, the preparing of the sensor matrix is performed such that the degree of coverage of the layer of binding molecules R200 on the conductive surface section 3 amounts to at least 80%, as above defined.

Optimally, also, in the case of the second and, in given cases, additional preparation steps, in the case of which one or more preparation steps, the receptors are bound on the binding layer, the length(s) of time, during which the second and, in given cases, other preparation solutions is/are led through the measurement duct, is/are so selected, that, in each case, a degree of coverage of 80%, as above defined, is achieved.

As shown in FIGS. 1*a*) and *b*), the layer structure of the sensor matrix and, in given cases, the direct or indirect binding of marker bearing molecules on the analyte or on target molecules competing with the analyte for binding locations of the sensor matrix permits, in simple manner, the transfer of technology of methods known from laboratory use for single-use assays to a method executable repeatedly and automatically by means of a bioanalyzer. Described as an example of this here is the transfer of an immunoassay for single-use laboratory execution to an automatically working bioanalyzer for process measurements technology: In the laboratory assay, the receptor layer is produced by adsorption of antibodies against the bovine corona virus (BCV) onto the hydrophobic substrate surface of a microtiter plate. Then, the measurement sample, which is to be examined for BCV-components, is applied and subsequently rinsed, so that BCV not bound on the receptors is removed. Thereafter, a second antibody against another epitope of the BCV is applied, rinsed anew and then a conjugate of a horseradish peroxidase (HRP)-conjugated, third antibody applied. This third antibody binds on the second, so that such is indirectly marked with HRP. After repeated rinsing, there occurs subsequently the determining of the measured value by a final step of addition of the chromophoric substrate, 2,2'-azino di-(3-ethyl-benzthiazoline) 6-sulphonic acid (ABTS) and hydrogen peroxide and photometric determining of the absorption of this solution.

A method for transfer of the determination of BCV content of a liquid sample by means of the described single-use, affinity bioassay to an automated and repeatedly performable, in situ determination of the BCV content of a liquid sample by means of a bioanalyzer will now be described. In a first step (step a), a suitable binding structure for the construction of the binding layer, or binding layers, of the sensor matrix is to be selected. Since the antibody against BCV (anti BCV) serving as receptor R350 concerns a non-biotinylated antibody of the class IgG, the FIG. 1*b*)

based, layer sequence thiol-PEG-biotin-Neutravidin biotin-anti-IgG-anti-BCV is quite suitable, wherein anti-BCV serves as receptor R350. As an alternative determination method (step b), in the case of application of an HRP molecule as marker bearing molecule R500, besides the chromophoric ABTS reaction with following photometric determination, also the chemiluminescent reaction between luminol and hydrogen peroxide can be used. This has, in an automated bioanalyzer, the advantage that only one photodetector, such as, for example, a photodiode, is required as signal transducer.

In an additional step, a suitable blocking reagent is selected for the materials used in the automated bioanalyzer for liquid lines or other parts coming in contact with the liquid sample or the other used reagents, in order to reduce the unspecific adsorption of the components.

After in this way, the binding layer, or binding layers, has/have been defined and an alternative determination method selected, there results a binding layer sequence of the sensor matrix selected from a few, universal, standard variants and formed from:

a thiophilic substrate (substrate 3)

thiol-PEG-biotin (first binding molecules R200 with biotin as functional group for indirect binding of the receptor R350 via second binding molecules R310)

Neutravidin (molecules binding on the binding molecules R200 R300 and on which the second binding molecules R310 are bound)

biotin-anti-IgG (second binding molecules R310).

On this binding layer sequence there then follows for the detection of a BCV content in a liquid sample the layer sequence of the affinity assay known from the laboratory method:

antibody against BCV of the type IgG (receptor R350 bound on the second binding molecules)

BCV (analyte R400, wherein the occupation density depends on the concentration of the analyte in the liquid sample)

second antibody against BCV (for indirect binding of the marker bearing molecule R500)

third, HRP-marked antibody (R500) against the second antibody for chemiluminescent detection by means of luminol/H2O2.

In a following step, all used components must be checked for cross reactivity (step c), in order thereby to exclude a corruption of the measurement signals. For this, for example, the receptor layer can be successively constructed while omitting, in each case, one layer and the measurement signal determined, which, in the case of occurrence of a cross reactivity, amounts to a value markedly over zero. Furthermore, the density of the individual layers, preferably the primary binding layer, is to be set by cobinding a further component non-functionalized or non-reactive relative to the following layer.

If the automated bioanalyzer has a microfluidic duct system for liquid transport, including a measurement duct, in which the sensor matrix is formed and the analyte detection performed, additionally, the suitable volume flows, the concentrations of preparation solutions containing the chemical species used for forming the sensor matrix, and the lengths of time, during which the individual preparation solutions and, in given cases rinse solutions, are led through the measurement duct, are to be ascertained (step d). In such case, preferably the concentrations are selected to be high, the volume flows of the preparation solutions likewise high and the lengths of length of time long. In this way, it is assured that the individual components of the sensor matrix form under the given conditions—corresponding to the chemical equilibrium at this concentration—a layer almost completely covering the, in each case, thereunder lying layer. In such case, each component to be examined is varied relative to its concentration in the preparation solution, the volume flow rate and the length of time, during which the preparation solution is led through the measurement duct. The sensor matrix embodied under the, in each case, selected conditions is supplied with a measured solution with a known analyte concentration and, by means of the selected detection method, based on the signal transducer of the bioanalyzer, a measurement signal is registered. From the so obtained measurement signals, there results a matrix, from which the, in each case, optimal method parameters, concentration, volume flow rate and length of time of the leading through the measurement duct for each layer of the sensor matrix can be ascertained. Thus, for example, a combination can be selected, which enables an as short as possible leading of the preparation solution through the measurement duct and, in spite of this, enables a measurement signal of 95% of the measurement signal in the case of a very much longer duration of the leading through of the preparation solution. Through this systematic procedure, the matching of the said method parameters to a microfluidic flow through system can occur rapidly.

In an additional step, the method parameters for performing the regeneration, respectively clearing, of the substrate are to be determined in an analogous manner (step e). For this, first of all, it is established whether a cleaning by chemical means, for example, by leading a cleaning solution through the measurement duct for essentially complete clearing of the substrate will be sufficient, or whether an electrochemical cleaning should be executed, in the case of which, besides the leading of the cleaning solution through the measurement duct also the potential of the substrate relative to a counter electrode, respectively reference electrode, is varied in such a manner that, in given cases, supported by hydrogen, respectively oxygen, formation by electrolysis of the cleaning solution, an at least partial decomposition of the sensor matrix, and, in given cases, molecules bound thereon, occurs. Using a series of tests, the method parameters, concentration/composition of the cleaning solution, potential of the substrate, respectively electrical current level of the electrical current flowing between substrate and counter electrode, length of time of the leading of the cleaning solution through the measurement duct, in given cases, length of time of the leading of auxiliary liquids through the measurement duct, curve of the substrate potential, respectively of the electrical current flowing between the substrate and the counter electrode can be varied, and, based on a measurement signal, which represents the degree of clearing of the substrate, the regeneration success can be determined. From a corresponding matrix, in which the cleaning success is plotted as a function of different process parameters, optimal method parameters can be determined.

Using samples from the corresponding area of application, when required, measurements are performed, in order, in given cases, to identify (step f) matrix effects resulting from the particular measured medium. Should these occur, suitable countermeasures for the particular case can be ascertained, such as, for example, dilution of the sample or taking into consideration the measured value deviations in the subsequent calibration of the method. After the affinity assay transferred to the automated in situ determination by means of a bioanalyzer has been calibrated, a corresponding validation occurs (step g). This includes reviewing storage stability of the preparation solutions and other applied reagents.

The advantage of the above described method is that affinity assays for quality control, for example, in a biotechnological production plant, applied in usual laboratory practice, for example, performed as a single-use, laboratory method, can be efficiently transferred to an automated bioanalyzer. Thus, it is, for example, possible, to analyze for the content of a substance, for example, a protein or, as in the above example, a vaccine, fully automatically, repeatedly and online. The application of one or a few standard layer systems for binding of almost any receptor and/or the application of one or a few marker bearing molecules offer a platform, or construction kit, solution, to which, in the described manner, known laboratory methods can be transferred with relatively little effort.

The invention claimed is:

1. A method for automated in situ determining of an analyte content of a liquid sample using a bioanalyzer, the method comprising a repeatedly performable sequence of steps as follows:
   (i) preparing a sensor matrix said sensor matrix comprising a plurality of receptors, which form a terminating receptor layer of said sensor matrix and which bind the analyte and/or further target molecules, or bring about a chemical conversion of the analyte or of the further target molecules, wherein said preparing of the sensor matrix includes leading through a measurement duct of a microfluidic system of the bioanalyzer a preparation solution of at least a first chemical species, which include at least one first functional group binding on a substrate of the measurement duct and at least one second functional group, wherein an amount of the first chemical species of the preparation solution are bound on the substrate via the at least one first functional group binding on the substrate, and wherein the at least one second functional group of the amount of the first chemical species bound on the substrate serves as said plurality of receptors or for subsequent binding of said plurality of receptors;
   (ii) leading the liquid sample, or a liquid to be measured obtained by treating the liquid sample with at least one reagent, through the measurement duct, wherein the analyte contained in the liquid sample or in the liquid to be measured, and/or the further target molecules contained in the liquid sample or the liquid to be measured, binds on the plurality of receptors or are chemically converted by the plurality of receptors, and determining a measured variable correlated with the amount of the further target molecules bound or converted by the plurality of receptors or with the amount of the analyte bound or converted by the plurality of receptors and deriving therefrom the analyte content of the liquid sample; and
   (iii) clearing the substrate, wherein the clearing includes continuously leading an aqueous electrolyte through the measurement duct and effecting an electrical current flow between the substrate and a counter electrode through the aqueous electrolyte,
   wherein the effecting of the current flow includes, during the leading of the aqueous electrolyte through the measurement duct, controlling an electrical potential of the substrate alternately between negative values of −0.5 V to −1.25 V and positive values of +1.5 V to +2.25 V relative to an Ag/AgCl-reference electrode, such that the sensor matrix is alternately exposed to oxidizing and reducing conditions yielding oxygen and hydrogen formation, respectively, whereby the sensor matrix, including the analyte and any of the further target molecules bound thereto, are released from the substrate, wherein the substrate comprises a metal material.

2. The method as claimed in claim 1, wherein the counter electrode is embodied in the measurement duct opposite to the substrate or coaxially with the substrate, as another substrate, on which binds the functional group of the first chemical species binding on the substrate.

3. The method as claimed in claim 1, wherein the substrate comprises a thiophilic, electrically conductive substrate and the functional group of the first chemical species binding on the substrate comprises a thiol, or disulfide, group, wherein a layer of the first chemical species is formed by binding of the sulfur atoms of the thiol, or disulfide, groups on the substrate.

4. The method according to claim 1, wherein during the electrical current flow, electrically conductive contact between the substrate and the counter electrode is established by the aqueous electrolyte, which contains cyanide ions or halogen ions in concentrations of less than 150 mmol/l.

5. The method as claimed in claim 1, wherein the potential of the substrate is varied continuously or discontinuously between a minimum value and a maximum value, in order to reclear the substrate by electrochemical cleaning, and/or the electrical current level of the electrical current flow produced between the substrate and the counter electrode is varied continuously or discontinuously, between a minimum value and a maximum value, in order to reclear the substrate by electrochemical cleaning.

6. The method as claimed in claim 1, wherein one or more cleaning liquids and/or one or more auxiliary liquids is/are led through the measurement duct, before, during or after the producing of the electrical current flow between the substrate and the counter electrode.

7. The method as claimed in claim 6, wherein during the effecting of the electrical current flow between the substrate and the counter electrode, an acidic phosphate buffer solution is led as the aqueous electrolyte through the measurement duct, the aqueous electrolyte including $Na_2SO_4$ or $H_2O_2$.

8. The method as claimed in claim 7, wherein the acidic phosphate buffer solution includes a peroxide.

9. The method as claimed in claim 1, wherein the sequence of steps (i)-(iii) are performed in situ repeatedly and directly one after the other at least 50 times.

10. The method as claimed in claim 1, the method further comprising:
   during or following the clearing, checking the substrate for residual components of the sensor matrix by means of an electrochemical measuring method, an optical measuring method or an adsorption test, or by measuring electrical current level during the clearing.

11. The method as claimed in claim 1, wherein during the leading of the liquid sample or the liquid to be measured obtained by treating the liquid sample with at least one reagent through the measurement duct, the analyte contained in the liquid sample, or in the liquid to be measured and/or other target molecules contained in the liquid sample or the liquid to be measured, binds selectively and specifically on the plurality of receptors.

12. The method as claimed in claim 1, wherein the Ag/AgCl-reference electrode is in conductive contact via the aqueous electrolyte via an electrolyte bridge.

13. The method as claimed in claim 1, wherein the electrical potential of the substrate in reference to a reference potential is varied linearly between a minimum value and a maximum value.

14. The method as claimed in claim 1, wherein the sensor matrix comprises a receptor layer including the plurality of first chemical species bound on the substrate via their first functional group and the second functional group of said plurality of first chemical species bound on the substrate serving as said plurality of receptors.

15. The method as claimed in claim 1, wherein the sensor matrix further includes one or a plurality of binding layers, wherein the plurality of first chemical species bound on the substrate via their first functional group forms a first binding layer, and wherein the preparing of the sensor matrix further comprises, after the leading through the measurement duct of said preparation solution of the first chemical species and passing through the measurement duct an additional preparation solution, or several additional preparation solutions sequentially, each additional preparation solution including chemical species forming an additional binding layer of the sensor matrix, and binding the plurality of receptors on an outermost binding layer of the sensor matrix to form the terminating receptor layer.

16. The method as claimed in claim 1, where in the metal material is gold and/or platinum.

* * * * *